(12) United States Patent
Munoz et al.

(10) Patent No.: US 10,518,133 B2
(45) Date of Patent: Dec. 31, 2019

(54) DEVICE POWER SAVING DURING EXERCISE

(71) Applicant: Polar Electro Oy, Kempele (FI)

(72) Inventors: David Munoz, Tampere (FI); Mikko Tuunanen, Oulu (FI); Matti Korpela, Oulu (FI); Markku Karjalainen, Kempele (FI); Jarmo Torvinen, Oulu (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 16/166,110

(22) Filed: Oct. 21, 2018

(65) Prior Publication Data
US 2019/0056777 A1    Feb. 21, 2019

Related U.S. Application Data

(63) Continuation of application No. 15/446,430, filed on Mar. 1, 2017, now Pat. No. 10,146,297, which is a
(Continued)

(51) Int. Cl.
*G06F 9/44*    (2018.01)
*G06F 1/32*    (2019.01)
(Continued)

(52) U.S. Cl.
CPC ........ *A63B 24/0087* (2013.01); *A61B 5/0205* (2013.01); *A61B 5/1118* (2013.01); *A61B 5/4806* (2013.01); *A61B 5/681* (2013.01); *A61B 5/7465* (2013.01); *G06F 1/3228* (2013.01); *A61B 5/01* (2013.01); *A61B 5/1112* (2013.01); *A63B 22/02* (2013.01);
(Continued)

(58) Field of Classification Search
CPC ......... G06F 1/3203; G06F 3/0634; G06F 1/32
USPC ...................... 713/300, 320, 323
See application file for complete search history.

(56) References Cited

U.S. PATENT DOCUMENTS 5,671,442 A    9/1997 Feeny et al.
7,789,800 B1   9/2010 Watterson et al.
(Continued)

FOREIGN PATENT DOCUMENTS

EP    1968028 A1    9/2008

OTHER PUBLICATIONS

International Search Report and Written Opinion, Application No. PCT/EP2014/054350, 9 pages, dated Nov. 4, 2014.
(Continued)

*Primary Examiner* — Michael J Brown
(74) *Attorney, Agent, or Firm* — FisherBroyles, LLP

(57) ABSTRACT

A method includes: supporting a normal operation mode during which functionalities of a portable apparatus are available through an operating system of the apparatus, wherein the operating system includes a plurality of layers including a kernel and library functions-layer; supporting a limited operation mode during which the apparatus is configured to execute a physical activity algorithm based on physical activity data corresponding to a physical activity session performed by a user of the apparatus, wherein the physical activity algorithm applies a direct low-level hardware access bypassing at least the layers above the kernel and the library functions-layer; and switching between the normal operation mode and the limited operation mode.

21 Claims, 8 Drawing Sheets

Related U.S. Application Data continuation of application No. 14/438,776, filed as application No. PCT/EP2014/054350 on Mar. 6, 2014, now Pat. No. 9,612,650.

(51) Int. Cl.

| | |
|---|---|
| *A61B 5/02* | (2006.01) |
| *A63B 24/00* | (2006.01) |
| *G06F 1/3228* | (2019.01) |
| *A61B 5/00* | (2006.01) |
| *A61B 5/0205* | (2006.01) |
| *A61B 5/11* | (2006.01) |
| *G06F 9/4401* | (2018.01) |
| *A61B 5/01* | (2006.01) |
| *A63B 71/06* | (2006.01) |
| *A63B 22/02* | (2006.01) |
| *A63B 22/06* | (2006.01) |

(52) U.S. Cl.
CPC ....... *A63B 22/0605* (2013.01); *A63B 71/0622* (2013.01); *A63B 2220/12* (2013.01); *A63B 2220/17* (2013.01); *A63B 2220/20* (2013.01); *A63B 2220/30* (2013.01); *A63B 2220/40* (2013.01); *A63B 2220/51* (2013.01); *A63B 2220/72* (2013.01); *A63B 2220/75* (2013.01); *A63B 2220/803* (2013.01); *A63B 2220/805* (2013.01); *A63B 2220/833* (2013.01); *A63B 2220/836* (2013.01); *A63B 2220/89* (2013.01); *A63B 2225/20* (2013.01); *A63B 2225/50* (2013.01); *A63B 2230/01* (2013.01); *A63B 2230/06* (2013.01); *A63B 2230/50* (2013.01); *A63B 2230/75* (2013.01); *G06F 9/4411* (2013.01); *G06F 9/4418* (2013.01)

(56) References Cited

U.S. PATENT DOCUMENTS

| | | |
|---|---|---|
| 9,612,650 B2 | 4/2017 | Munoz |
| 10,146,297 B2 * | 12/2018 | Munoz ................ G06F 1/3228 |
| 2008/0263324 A1 | 10/2008 | Sutardja et al. |
| 2010/0235667 A1 | 9/2010 | Mucignat et al. |
| 2012/0116548 A1 | 5/2012 | Goree et al. |

OTHER PUBLICATIONS

Anonymous: "Bluetooth Low Energy Wireless Technology Backgrounder", Nordic Semiconductor, XP-002711878, pp. 1-8, 2011.

International Search Report for corresponding PCT Application No. PCT/EP2012/073823, 3 pp, dated Nov. 9, 2013.

* cited by examiner

DEVICE POWER SAVING DURING EXERCISE

CROSS-REFERENCE TO RELATED APPLICATIONS

This application is a continuation application of pending U.S. application Ser. No. 15/446,430, filed Mar. 1, 2017, which is a continuation application of U.S. application Ser. No. 14/438,776, filed Apr. 27, 2015, which issued as U.S. Pat. No. 9,612,650 on Apr. 4, 2017, which is a National Stage application of International Application No. PCT/EP2014/054350, filed Mar. 6, 2014, which are incorporated by reference herein in their entireties.

BACKGROUND

Field

The disclosed subject mater relates generally to power saving of an exercise device during an exercise.

Description of the Related Art

Nowadays portable apparatus, such as smart watches, are used for recording physical activities performed by the person carrying the apparatus. These apparatuses may run a generic operating system platform, such as an Android or iOS, thus enabling third party software applications to be installed and executed. However, these operating systems are usually optimized for smart phones or tablet computers which may have larger battery capacity. Therefore, their usability in, e.g. smart watches, is considerably reduced by the short use time due to smaller battery capacity.

However, in a long-lasting operation, such as during an exercise, it may be critical that the portable apparatus does not run out of battery during the exercise. Thus, the way the portable apparatus consumes power during the exercise is critical.

SUMMARY

According to an aspect of the claimed subject matter, there is provided a portable apparatus, comprising: at least one processing unit and at least one memory including a computer program code, wherein the at least one memory and the computer program code are configured, with the at least one processing unit, to cause the portable apparatus to perform operations comprising: supporting a normal operation mode during which functionalities of the apparatus are available through an operating system of the apparatus, wherein the operating system comprises a plurality of layers including a kernel and library functions-layer; supporting a limited operation mode during which the apparatus is configured to execute a physical activity algorithm based on physical activity data corresponding to a physical activity session performed by a user of the apparatus, wherein the physical activity algorithm applies a direct low-level hardware access bypassing at least the layers above the kernel and the library functions-layer; and switching between the normal operation mode and the limited operation mode.

According to another aspect of the claimed subject matter, there is provided a method, comprising: supporting a normal operation mode during which functionalities of the apparatus are available through an operating system of the apparatus, wherein the operating system comprises a plurality of layers including a kernel and library functions-layer; supporting a limited operation mode during which the apparatus is configured to execute a physical activity algorithm based on physical activity data corresponding to a physical activity session performed by a user of the apparatus, wherein the physical activity algorithm applies a direct low-level hardware access bypassing at least the layers above the kernel and the library functions-layer; and switching between the normal operation mode and the limited operation mode.

According to another aspect of the claimed subject matter, there is provided a computer program product embodied on a distribution medium readable by a computer and comprising program instructions which, when loaded into an apparatus, execute a method comprising: supporting a normal operation mode during which functionalities of the apparatus are available through an operating system of the apparatus, wherein the operating system comprises a plurality of layers including a kernel and library functions-layer; supporting a limited operation mode during which the apparatus is configured to execute a physical activity algorithm based on physical activity data corresponding to a physical activity session performed by a user of the apparatus, wherein the physical activity algorithm applies a direct low-level hardware access bypassing at least the layers above the kernel and the library functions-layer; and switching between the normal operation mode and the limited operation mode.

BRIEF DESCRIPTION OF THE DRAWINGS

In the following, the disclosed subject matter will be described in greater detail with reference to the embodiments and the accompanying drawings, in which.

DETAILED DESCRIPTION

The following embodiments are exemplary. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Figure 1:
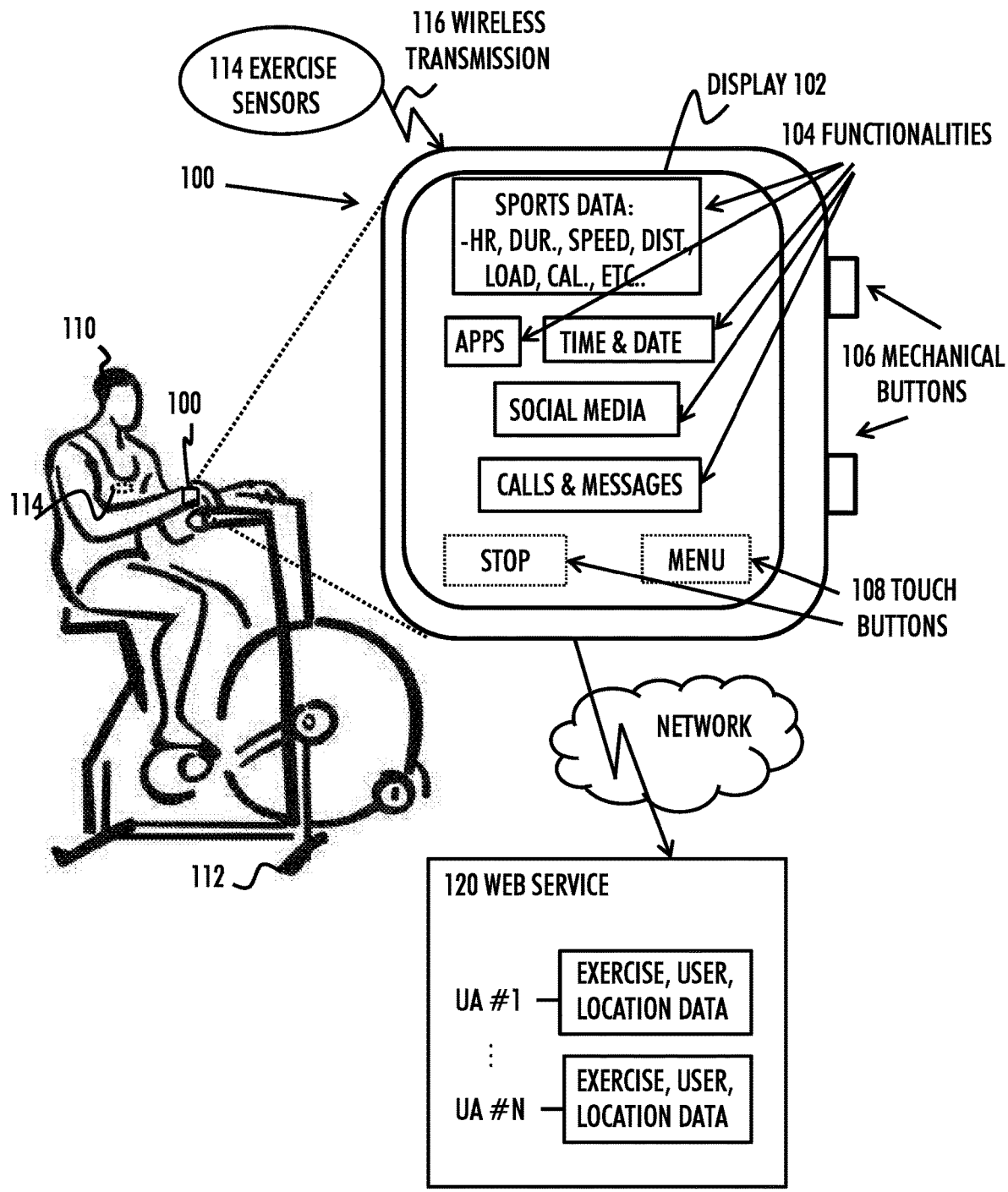
FIG. 1 presents a system, according to an embodiment.

As shown in FIG. 1, it is common to wear a personal training computer (TC) 100 during an exercise. The training computer 100 may be a wrist worn device, such as a smart watch. From the training computer 100, the exerciser 110 may monitor training parameters that characterize the physiological state during the exercise in real time. The physiological state may be detected from one or more performance metrics, such as by monitoring how the heart rate changes as the training session goes on.

In order to enable such monitoring, the training computer 100 may receive information from one or more physiological exercise sensors 114 worn by the user 110, such as heart rate-related information from a heart activity sensor (based e.g. on optical, electrical and/or pressure sensing), location specific information from a stride sensor or from a global positioning system (GPS) receiver, pace/speed related data from the GPS/stride sensor. Furthermore, sensors 114 may be installed in the exercise device 112, in case such is applied during the exercise. These sensors 114 integrated on the device 112 may comprise for example power sensors, distance sensors and cadence sensors.

In an embodiment, the training computer 100 comprises at least one physiological exercise sensor 114, such as the GPS receiver and/or an optical heart activity sensor. However, in an embodiment, at least one physiological exercise sensor 114 is an external sensor and not integrated in the training computer 100. The transfer of the exercise data from the external exercise sensors 114 to the training computer 100 may be performed wirelessly via a wireless link 116. The wireless communication link 116 may apply, e.g., WiFi, Bluetooth, Bluetooth low energy (BLE), or cellular network connection, to mention only a few possible options.

The following is a non-limiting list of possible types of exercise data (also known as physiological sensor data or as physical activity data) that may be detected by the sensor 114 or that the training computer 100 may determine on the basis of exercise data from the sensors 114: heart rate zones, heart rate samples, heart rate variation samples, heart beat interval samples, fat consumption rate, calorie consumption rate, consumed amount of calories, activity zones, activity samples, speed and/or pace samples, power samples, cadence samples, altitude samples, temperature samples, location samples, distance elapsed, time elapsed, pedal index, left-right balance, running index, training load, galvanic skin response samples, fluid balance, skin temperature samples, heading samples and/or bike angles. The location data may comprise satellite positioning data, such as, GPS positioning data, or any other data that allows the determination of the location of the exerciser during the exercise at any given time. The movement indoors may be detected via indoor location tracking methods, such as mapping techniques including measuring Earth's magnetic fields or radio frequency signals. The sensors 114 may comprise any sensors that are needed for detecting a given exercise data type, such as temperature sensor for detecting ambient temperature or skin temperature.

The training computer 100 may store the exercise data which the user (exerciser) 110 may use in post-analysis of the performed exercise. In an embodiment, the post-analysis is processed in the TC 100. In another embodiment, the exercise data is transferred from the training computer 100 and/or exercise sensor(s) 114 to a web service 120 located in a server of a network, and the post-analysis is carried out in the web service 120. In case the training computer 100 does not have a direct internet access capability, the training computer 100 may access the internet (e.g. the web service 120) via an external mobile phone coupled to the training computer 100, e.g., via a Bluetooth connection. The mobile phone may be associated to the same user 110 as the training computer 100.

The web service 120 may comprise exercise data user accounts (UA), each exercise data user account comprising exercise data associated with a specific user 110. As such, there may be different user accounts for different users (#1, #2, . . . , #N). An example of such a web service 120 may be a Polar Personal Trainer (PTT), Polar Flow or iFIT service which comprises a database for storing the plurality of user accounts. In an embodiment, the web service 120 may require that the users first connect to the web service 120 by applying a user name and a password, or other identification means. The training/exercise data at the user accounts may have been stored during or after the exercise. The user accounts may additionally store physiological data of the user and user attributes obtained from the exerciser and/or the exercise device, such as name, gender, age, weight, height, image, status, motto, fitness level, training schedule, maximum oxygen intake (VO2Max), maximum heart rate (HRMax), performance zones (heart rate zones, speed zones), aerobic and anaerobic thresholds.

The device 100 (e.g. a portable smart watch) comprises at least one processing unit and at least one memory including a computer program code, wherein the at least one memory and the computer program code are configured, with the at least one processing unit, to cause the device 100 to provide a variety of different functionalities 104, such as support for social media services (e.g. notifications), support for call and message indications (e.g. caller ID, incoming call/message notification), a variety of different applications (APPs), possible running on Android or iOS, or any other operating system that may enable such functionalities, for example. Further, there may be a display 102 with touch sensitive capabilities supporting touch buttons 108 in addition to mechanical buttons 106. These software and hardware (HW) functionalities of the device 100 may consume a significant amount of battery, for example during an exercise mode when multiple functionalities are simultaneously active.

However, as said, in a long-lasting operation, such as during a physical activity session (e.g. during an exercise), the power consumption of the device 100 is critical. In case the battery runs out before the end of the exercise, the user 110 may not be able to record all the exercise data throughout the training. This is not desired.

Figure 2A:
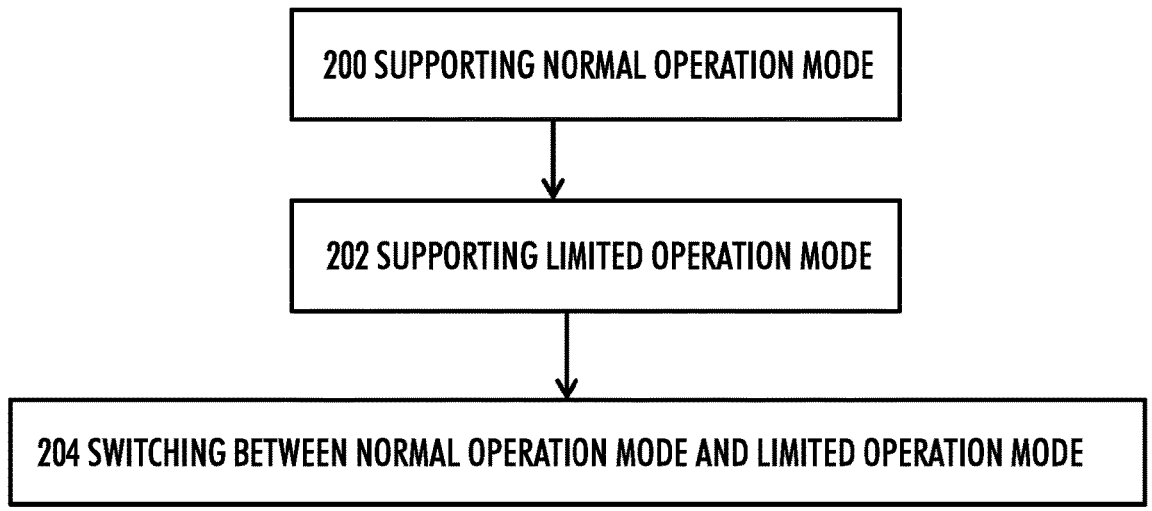
FIG. 2A show a method, according to an embodiment.
Figure 2B:
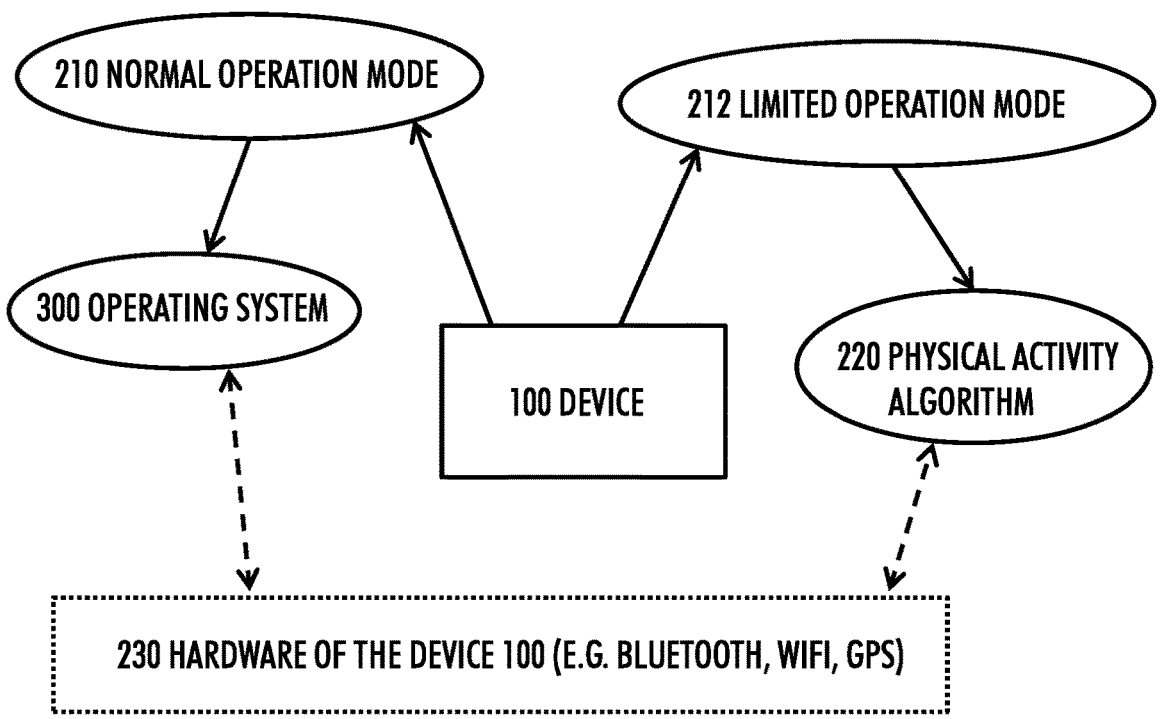
FIG. 2B shows that a device may operate in a normal operation mode or in a limited operation more, according to an embodiment.

Therefore, it is proposed, as shown in FIGS. 2A and 2B, that the device 100 supports a normal operation mode 210 and a limited operation mode 212, as illustrated with steps 200, 202. In order to optimize the power consumption of the device while providing all needed functionalities 104 to the user 110 of the device 100, the device 100 may in step 204 switch between the normal operation mode 210 and the limited operation mode 212. The power consumption of the device 100 during the limited (operation) mode 212 may be smaller for a given task than during the normal (operation) mode 210. Thus, the limited operation mode 212 may be used when smaller power consumption is needed and a smaller amount of available functionalities 104 is enough, whereas the normal operation mode 210 may be applied when larger set of functionalities 104 is needed.

In an embodiment, during the normal operation mode 210, the functionalities 104 of the device 100 are available through an operating system (OS) 300 of the device 100. The operating system 300 may comprise a plurality of layers including a kernel and library function-layer, as will be described later.

During the limited operation mode 212, the device 100 may execute at least a physical activity algorithm (PAA) 220 based on physical activity data corresponding to a physical activity session performed by the user 110 of the device 100. However, here the physical activity algorithm 220 may apply a direct low-level hardware access bypassing at least the layers of the operating system 300 which are above the kernel and the library function-layer.

On the contrary, the hardware access in the normal mode 210 may go through the plurality of layers of the operating system 300, as the application layer is typically on top the OS layer stack. Therefore, in case the PAA 220 was run in the normal operation mode 210, the PAA 220 would apply the plurality of layers of the operating system 300 for hardware access.

In an embodiment, the device 100 is a portable wrist-worn wrist device, such as a smart watch. In an embodiment, the device 100 is a sport watch. In an embodiment, the device 100 is a training computer.

Figure 3:
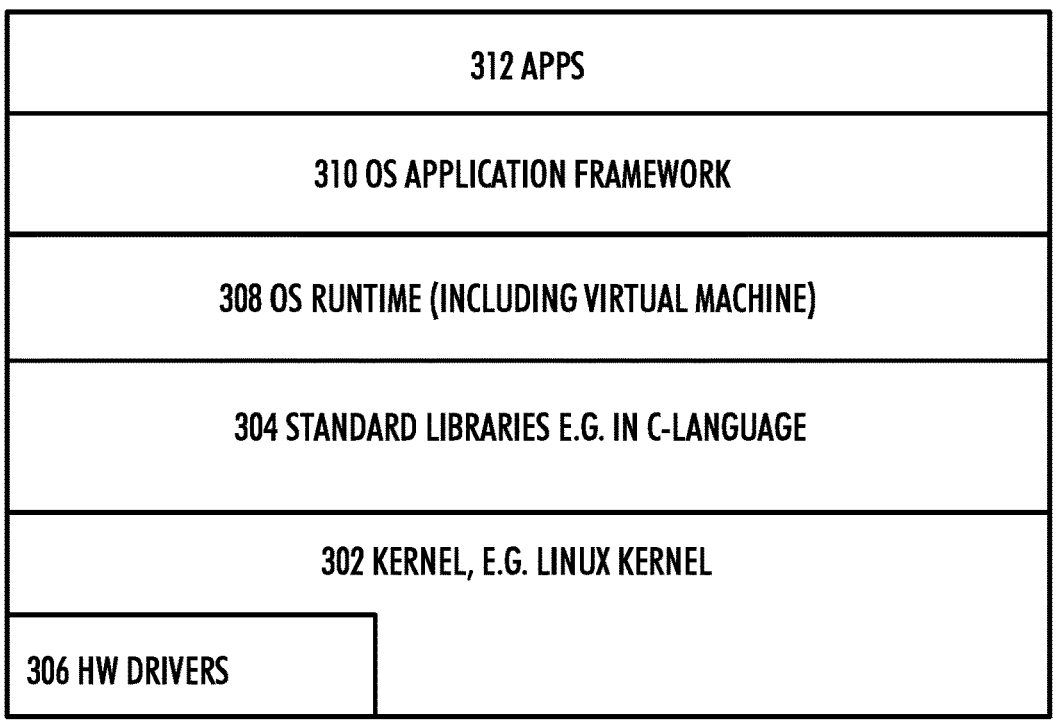
FIGS. 3 and 4 illustrate an operating system of the device, according to some embodiments

An example operating system 300 is shown in FIG. 3. As shown, the operating system 300 comprises a layered hierarchy. Although the operating system 300 may be any operating system, such as Android, iOS, BSD, Linux, OS X, QNX, Microsoft Windows, Windows Phone, or IBM z/OS, for the reasons of simplicity, the description will assume that the operating system 300 is Android.

Let us take a look at the layers of the example operating system 300. In an embodiment, the OS 300 is built on top of a kernel 302. In case of Android operating system 300, the kernel is a Linux kernel 302. The kernel 302 may be seen as the core of the operating system 300. The kernel 302 may comprise, e.g., memory management programs, security settings, and power management software.

The kernel 302 further provides access to the hardware 230 upon a request by an application, for example. In order to do this, the kernel 302 may comprise HW drivers 306. A hardware driver is a computer program that controls a particular type of hardware that is attached to the device. In an embodiment, the HW drivers 306 comprise a driver for the display 102. In an embodiment, the HW drivers 306 comprise a driver for a camera of the device 100. In an embodiment, the HW drivers 306 comprise a driver for enabling a Bluetooth and/or Bluetooth low energy communication to/from the device 100. In an embodiment, the HW drivers 306 comprise a driver for enabling a wireless local area network (WLAN/WiFi) communication to/from the device 100. In an embodiment, the HW drivers 306 comprise a driver for a flash memory drive of the device 100. In an embodiment, the HW drivers 306 comprise a universal serial bus (USB) interface of the device 100. In an embodiment, the HW drivers 306 comprise a driver for a user interface, such as mechanical keys/buttons, of the device 100. In an embodiment, the HW drivers 306 comprise a driver for audio output of the device 100. In an embodiment, the HW drivers 306 comprise a driver for a power management unit of the device 100. In an embodiment, the HW drivers 306 comprise a driver for a binder of an inter-process communication (IPC) interface of the device 100.

In an embodiment, the drivers required for running the PAA 220 during the limited operation mode 212 may comprise a driver for the display 102. In an embodiment, the drivers required for running the PAA 220 during the limited operation mode 212 may comprise a driver for enabling a Bluetooth and/or Bluetooth low energy communication. In an embodiment, the drivers required for running the PAA 220 during the limited operation mode 212 may comprise a driver for the WLAN/WiFi communication. In an embodiment, the drivers required for running the PAA 220 during the limited operation mode 212 may comprise a driver for a user interface. In an embodiment, the drivers required for running the PAA 220 during the limited operation mode 212 may comprise a driver for a power management unit. The kernel 302 may comprise some memory which is reserved for the parts of the operating system 300 that have to stay in the memory and may be off-limits to any other software. The device 100 may store, e.g., a Bootloader, such as uBoot or Fastboot. The bootloader may be a computer program that loads the main operating system 300 or runtime environment for the device 100.

The next level on top of the kernel 302 may be a standard library functions layer 304. The library functions 304 may comprise standard library instructions. The libraries 304 may comprise a set of instructions written e.g. on C or C++ language that tell the device 100 how to handle different kinds of data. Some of these libraries handle tasks related to graphics, multimedia codecs, database and browsers (e.g. WebKit). As an example, a media framework library supports playback and recording of various audio, video and picture formats.

An Android runtime layer 308 includes a set of core Java libraries. This layer may also include a virtual machine, such as a Dalvik virtual machine or Android Run Time (ART) in case of Android. The virtual machine is a software application that behaves as if it were an independent device with its own operating system. For example, the Android OS may use the virtual machine to run each application as its own process. This may be needed as native Android Java libraries are different from standard Java or Java Mobile Edition (JME) libraries. JME is an adaptation of Java Standard Edition to allow Java to run on embedded devices, such as mobile phones.

An application framework layer 310 may manage the device's 100 basic functions, such as e.g. resource allocation, switching between processes or programs and keeping track of the devices 100 physical location. At the top of the layer stack of the operating system 300 are the application layer 312, comprising one or more applications. This layer 310 may be seen as the layer with which the user 110 interacts with while being unaware of all the action taking place beneath this layer 310. Some applications are pre-installed on the device 100 while some may be downloaded from the Internet, such as from the Android market or a private store.

In an embodiment, there is only one operating system 300 in the device 100. In an embodiment, the operating system 300 is Android built on top of Linux kernel 302. In another embodiment, the operating system 300 is iOS built on top of XNU kernel 302. In an embodiment, the operating system 300 is Windows built on top of Windows 9x/NT kernel 302.

During the normal operation mode 210, the device 100 may access the full operating system 300 including all the layers of FIG. 3. However, running the Android, or any other operating system, may consume a significant amount of power. For example, running the Android 300 with the Linux kernel 302 may require e.g. 512 MB of memory. As such large amount of memory is needed, most power efficient memories may not be feasible due to high expenses. Therefore, cheaper, more power consuming memory types are used. Let us now take a look at different types memories used in computing devices.

Cache: Caches are designed to alleviate the bottleneck of slow memory access by making the data used most often by the processing unit readily available without accessing external main memory units. This may be accomplished by building a small amount of memory, known as primary or level 1 cache, into the processing unit. Typically, the size of the level 1 cache is small, ranging between 22 kilobytes (kB) and 128 kB. The secondary or level 2 cache is typically larger and resides on a memory card located near the processing unit. The level 2 cache may have a direct connection to the processing unit.

RAM: RAM stands for Random Access Memory. RAM is typically referred to as the main memory. RAM is a read/write-type of memory. It is considered fast and is used to store data and programs which a computer processor is currently processing and needs to have easily to hand. RAM is volatile in that it loses its contents when the power is switched off. The RAM may be beneficial because most data on computers is stored in slower "storage media" such as hard disks, solid state drives or flash memory. Therefore, the processing unit may need to copy the programs or data to be used into the RAM. Consequently, the higher the RAM size the faster is your computing device. However, RAM, and especially static RAM, is a relatively expensive memory type. There are two types of RAM, dynamic RAM (DRAM) and a static RAM (SRAM).

Dynamic RAM (DRAM) need to be refreshed frequently. It is not as expensive as SRAM but consumes more power for a given task.

Double data rate synchronous dynamic RAM (DDR SDRAM or simply DDR) is a type of DRAM. It is cheaper than SRAM, but consumes more power for a given task, at least partly because it is a capacitive memory.

SRAM (static RAM) may be used, e.g., as the cache memory. Unlike DRAM, SRAM does not have to be refreshed. Without the need for constant refreshing, SRAM may operate quickly. But the complexity of the memory unit may make it prohibitively expensive for use as the standard RAM. Further, SRAM may require only little power as no constant refreshing is needed. As an example, a given task performed with SRAM requires less power than the same task computed with DRAM. Static RAM may exists as integrated on a chip, such as on microprocessor units (MPU) and microcontroller units (MCU) as a dedicated RAM or as cache memory, or on application specific integrated circuits (ASICs).

ROM stands for Read Only Memory. It is non-volatile and used to store data which will not need to change, such as software to start up and run an electronic device or for the basic start-up functions of a device.

Flash memories are a type of non-volatile ROM memories. The flash memory may of a serial flash type. A serial is a low-power flash memory that uses a serial interface for sequential data access. When incorporated into an embedded system, serial flash requires fewer wires on the PCB than parallel flash memories, since it transmits and receives data one bit at a time. This may permit a reduction in board space, power consumption, and total system cost.

As DDR memories are cheaper than SRAM memories, they are typically used as the main RAM for driving the operating system 300 (such as Android+Linux kernel). This may consume a lot of power. In an embodiment, the normal operation mode 210 is defined as an operation mode during which the DDR memory of the device 100 are active. In an embodiment, during the normal operation mode 210, hardware access takes place through the layers of the operating system 300, including layers which are above the kernel 302 and the library function-layer 304.

Therefore, as shown in step 202 and 204, it may be advantageous to switch into the limited operation mode 212 of the device 100, in which the hardware access does not go through all the layers of the operating system 300 but applies the direct low-level hardware access between the PAA 220 and the predetermined hardware required by the PAA 220.

In an embodiment, the direct low-level hardware access comprises an access between a predetermined set of hardware and one of the following: a kernel of the operating system and the at least one processing unit. Thus, in an embodiment, the PAA 220 accesses the HW 230 via the kernel 302. As said, the kernel 302 may have direct access to the device drivers 306 for controlling the HW 230. In one embodiment, however, the kernel 302 may be inactive. In such case, the direct low level HW access may take place directly between the processing unit executing the PAA 220 and the HW 230 via the device drivers 306.

The predetermined set of hardware 230 that may need to be accessed during the execution of the PAA 220 may include e.g. communication enabling HW, such as Bluetooth (BLT), Bluetooth low energy (BLE), and/or WiFi, for reception of sensor data from external sensors, and location tracking enabling HW, such as a GPS receiver, for receiving location tracking data, to mention only a few non-limiting examples. Further, in an embodiment, near field communication (NFC)/radio frequency identification (RFID) may be activated.

In an embodiment, the device 100 may inactivate at least predetermined layers of the operating system 300 when entering the limited operation mode 212. These layers of the operating system 300 may comprise at least the layers above the library functions-layer 304, as shown with dots in FIG. 4. However, in an embodiment, all the layers above the kernel 302 are switched off (inactivated). Yet, in one embodiment, all the layers, including the kernel 302, are inactivated. In an embodiment, during the limited operation mode 212, at least the applications layer 312 is inactivated. In an embodiment, during the limited operation mode 212, at least the application framework layer 310 is inactivated. In an embodiment, during the limited operation mode 212, at least the OS runtime layer 308 is inactivated. In an embodiment, during the limited operation mode 212, at least the library functions layer 304 is inactivated. In an embodiment, during the limited operation mode 212, at least the kernel layer 302 is inactivated. Switching off at least some of the layers and at least partly inactivating the operating system 300 may provide for reduced power consumption. This may be, e.g., because the high-power consumption memory units, such as the DDR memory, may be switched off.

In an embodiment, the clock frequency of the device 100 is decreased for the limited operation mode 212 so as to decrease the power consumption rate.

Figure 4:
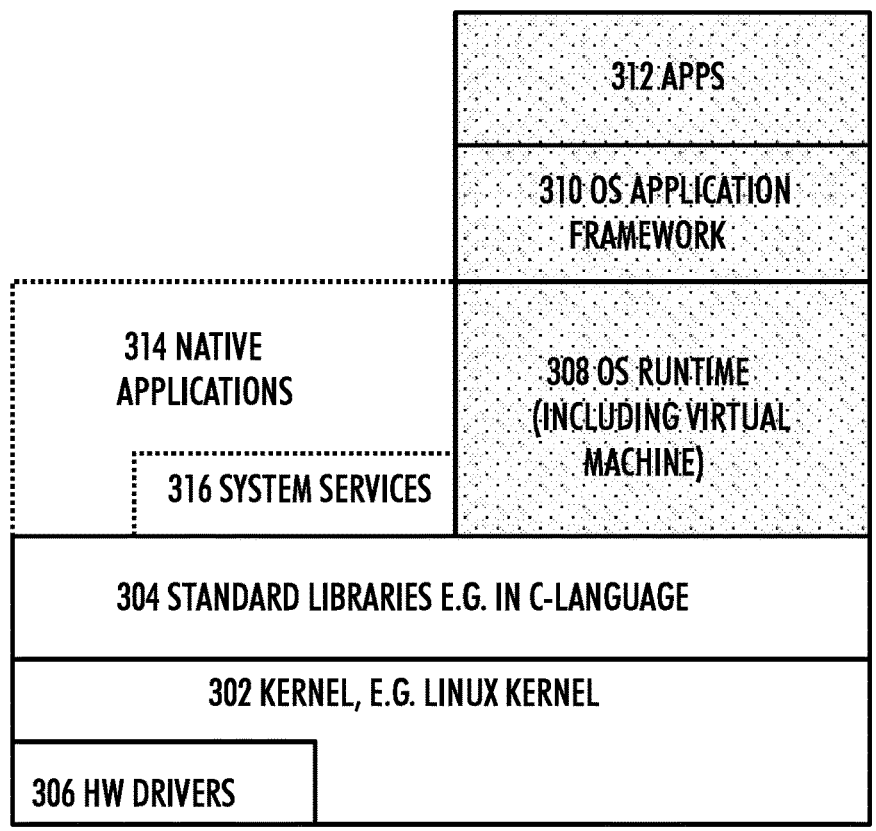

FIG. 4 also shows how native applications 314 and system services 316 may be located in the hierarchy of the OS 300. Native applications 314 may comprise software which is arranged to be run by the specific operating system, in this case for the Android OS 300. Because the native applications are written for a specific platform, they may interact with the operating system features and other software that is typically installed on that platform. For example, the native application 308 may use device-specific hardware and software. A native application may be pre-stored on the device 100 or it can be downloaded from a public or private store and installed on the device 100.

System services 316 may comprise necessary services for the operation of the device 100. There may include services, such as program execution e.g. for allocating and de-allocating memory, CPU scheduling in case of multi-tasking, I/O operation handling e.g. for providing input/output to applications, file system manipulation e.g. for writing data into new files or input taken from some files, communication handling e.g. for enabling communication between different processes, and error detection e.g. for monitoring the system for errors.

As shown in FIG. 4, these layers 314 and 316 are on the same level as the OS runtime layer 308. However, these native applications 314 may be run, with the aid of system services 316, without needing to operate the full OS 300 of the device 100.

In an embodiment, a set of functionalities of the apparatus is available to the apparatus during the normal operation mode 210 and only a predetermined subset of the functionalities is available to the apparatus during the limited operation mode 212. Therefore, switching some of the layers off may denote that the set of functionalities available to the user is larger in the normal operation mode 210 than in the limited operation mode 212. For example, applications locating in applications layer 312 of the operating system 300 may be inaccessible during the limited mode 212. These may include e.g. web applications downloaded to the device 100. However, the user may desire to use the full set of applications. Therefore, it is not feasible to apply the limited operation mode with a lower power consumption rate constantly. It may be noted though that the same functions run during the limited mode 212 may also be run in the normal operation mode 210. However, the application for providing the functionality may be different. In the limited mode it may be provided by the PAA 220, whereas in the normal mode the functionalities of the PAA 220 may be provided by another application, such as an Android application. The power consumption for a given task during the normal mode 210 may be higher than the power consumption for the same task during the limited mode 212. Thus, the switch between the two modes 210 and 212 in step 204 may be made in order to optimize the power consumption of the device 100, yet taking into account the needs of the user 110 of the device 100.

Figure 5:
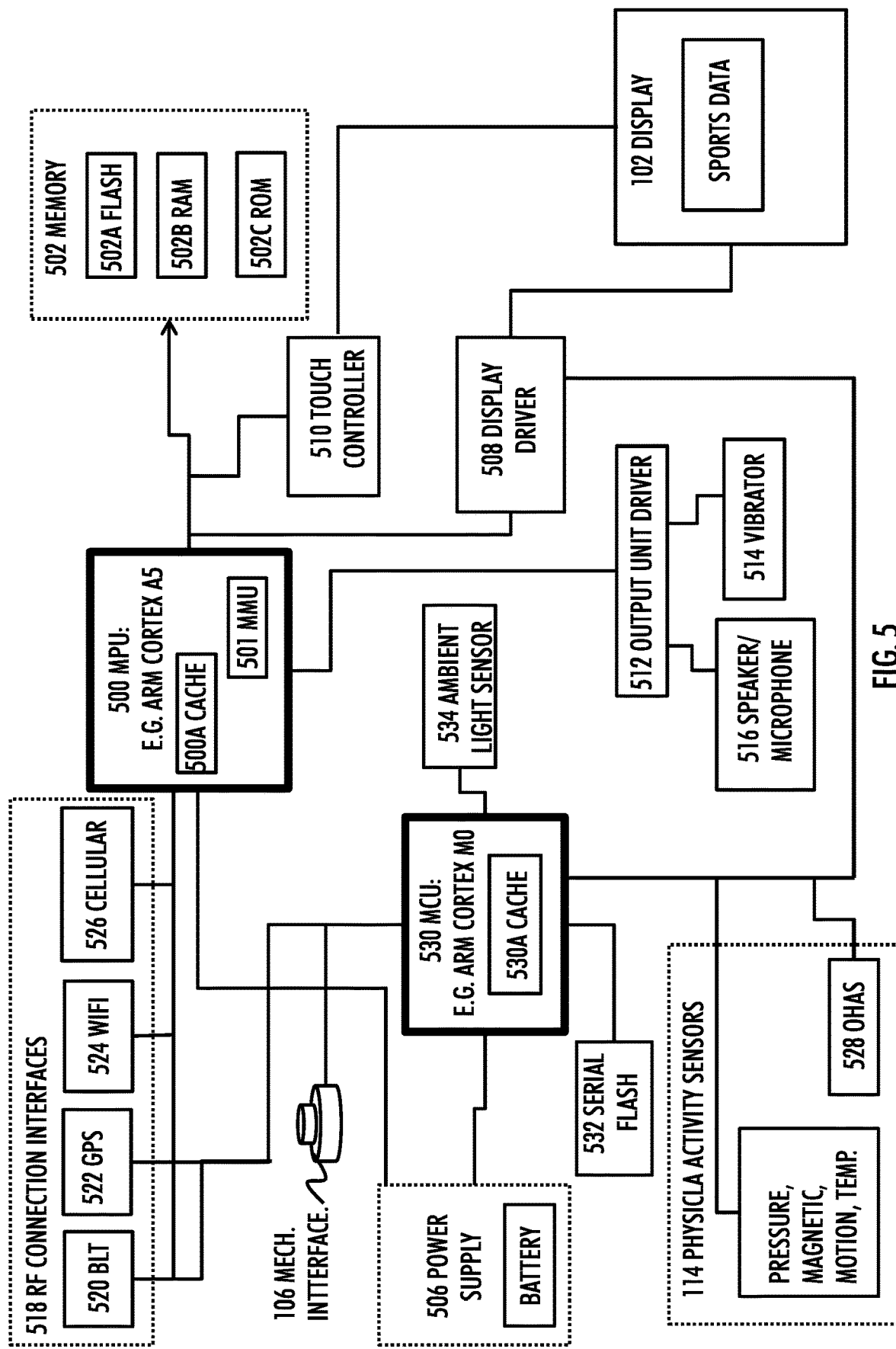
FIG. 5 depicts hardware configuration of the device, according to an embodiment.

Let us next look at example hardware architecture of the device 100 with reference to FIG. 5. The device 100 may comprise a microprocessor unit (MPU) 500, also known as the central processing unit (CPU). In an embodiment, the model of the MP 500 may be, e.g. ARM cortex A5.

The MPU 500 may comprise integrated memory 500A (such as SRAM which is relatively expensive but has relatively low power consumption rate) for relatively fast execution of functionalities with relatively low power consumption. In an embodiment, the integrated memory 500A is used as cache memory. However, there may be other purposes for the integrated memory 500A, as will be described.

Further, the MPU may access a memory unit 502 comprising, e.g., non-volatile flash memory 502A, which may be used for storing files/data that is often referenced, but rarely modified, such as application and operating system executable files. The flash memory 502A may be of serial type. In an embodiment, upon booting of the device 100, the MPU 500 may read the data on the flash drive in order to find the operating system data required for triggering the operation system on. This may provide for faster booting than via the normal ROM 502C. The memory unit 502 may further comprise volatile RAM memory 502B, such as DDR memory which is relatively cheap but has relatively high-power consumption. The size of the RAM may be, e.g. 128 MB (megabytes). Finally, the memory unit 502 may comprise non-volatile ROM memory 502C, which may have a size of a few gigabytes (GB). The memory unit 502 may store data related to user applications and data required for activating the operating system 300 of the device 100.

The device 100 may comprise a power supply 506, including a disposable battery or a rechargeable battery. The power supply 506 may have a limited power capacity and after the battery has run out of power, it needs to be replaced or recharged. In an embodiment, the battery is a lithium polymer (LiPo) battery. The power supply 506 may provide power for the MPU 500 and for the other hardware of the device 100. In an embodiment, the power supply 506 may at least partially recharge itself on the basis of motion or solar power, for example. The power supply 506 may also comprise power management unit The MPU 500 may connect to HW 230 via the operating system's kernel 302. In an embodiment, the MPU 500 may be coupled to the display 102 of the device 100 via a display driver 508. In an embodiment, the display 102 may be a touch sensitive display, wherein the touch sensitive functionality may be controlled (e.g. activated/inactivated) by the MPU 500, possibly via a touch controller 510.

In an embodiment, the MPU 500 may be coupled to an output driver 512. The output driver 512 may control, e.g. a vibrator 514 for causing vibration motion of the device 100 and/or a speaker 516 for outputting audio signals from the device 100. There may also be a microphone in the device 100 for reception of audio commands from the user. The output driver 512 may also provide an electric pulse to the skin of the user 110.

In an embodiment, the MPU 500 may connect to radio frequency (RF) connection interfaces 518. These may be used for providing connection capabilities for the device 100. In an embodiment, the device 100 comprises a BLT or BLE interface 520 for providing communication capabilities to/from the device 100 via BLT/BLE technique. In an embodiment, the device 100 comprises a GPS receiver 522 for receiving GPS signal in order to perform location tracking of the device 100. In an embodiment, the device 100 comprises a WiFi interface 524 for communication on WLAN or in wireless personal area network (WPAN). In an embodiment, the device 100 comprises a cellular interface 526 for performing communications via a cellular access. A skilled person may understand that the device 100 may comprise also other communication interfaces, such as interfaces based on ANT or ANT+ by Dynastream. Other device-to-device communication protocols are equally possible.

The device 100 may connect via the RF connection interface 518 to a mobile phone carried by the user 110 so as to communicate with the mobile phone. For example, the mobile phone may send notifications to the device 100, such as a wrist device, regarding incoming email, calls, messages, social media updates.

In an embodiment, the device 100 comprises physical activity sensors 114. In an embodiment, the physical activity sensors 114 comprise an optical heart activity sensor (OHAS) 528 for optically measuring the heart activity of the user 110. As an alternative or in addition to, the heart activity detection may take place electrically in which case the device 100 may receive heart activity data may be received via one of the RF connection interfaces 518 from the electrical heart activity sensor. In an embodiment, the physical activity sensors 114 comprise an accelerometer for determining motion of the device 100. The accelerometer may be a three-dimensional accelerometer capable of detecting motion in each direction of a three-dimensional coordinate system. In an embodiment, the physical activity sensors 114 comprise a gyroscope for further detecting motion and/or orientation of the device 100. In an embodiment, the physical activity sensors 114 comprise a magnetic sensor (e.g. a three-axis magnetometer) for detecting orientation of the device 100 on the basis of earth magnetic fields. In an embodiment, the physical activity sensors 114 comprise a pressure sensor for detecting ambient pressure. This may indicate the height information, e.g. with respect to predetermined level such as sea level. In an embodiment, the physical activity sensors 114 comprise a temperature sensor for determining ambient and/or device's internal temperature. Other physical activity sensors may be available as well, such as an ambient light sensor, a humidity sensor, and/or an electric field sensor on the screen. These additional sensors may be, as said earlier, worn by the user 110 or integrated into an exercise device, such as on a treadmill or on a bicycle, in which cases the physical activity data may be received via the RF connection interfaces 518 from the corresponding physical activity sensor. In an embodiment, although not shown in FIG. 5, the device 100 may comprise a proximity sensor for sensing the proximity of the device 100 with another device.

In an embodiment, the device 100 further comprises a microcontroller unit (MCU) 530. In an embodiment, the MCU 530 may be of an ARM cortex M0 type. In an embodiment, unlike the MPU 500, the MCU 530 may not be equipped with a memory management unit (MMU) 501. The MMU 501 is a computer hardware unit having all memory access passed through itself. Therefore, the MMU 501 may perform the translation of virtual memory addresses to physical addresses. For example, Linux kernel 302 may require the MMU to operate. As a result, in an embodiment, the MPU 500 may be able to drive the kernel 302, whereas the MCU 530 is not able drive the kernel 302. As the kernel 302, such as the Linux kernel is not run on the MCU 530, the MCU 530 may not be able to run the Android operating system 300, for example, whereas the MPU 500 may run the Android operating system 300.

The MCU 530 may be seen as a chip which is used to control the device at least partially. It is a type of microprocessor emphasizing self-sufficiency and cost-effectiveness, in contrast to a general-purpose MPU 500. In an embodiment, the MCU 530 may comprise all the memory and interfaces needed for a predetermined application(s), whereas the MPU 500 typically requires additional chips to provide these functions.

In an embodiment, the MCU 530 may comprise integrated memory 530A for data storage. The integrated memory 530A may be an internal memory integrated within the MCU 530. In an embodiment, the integrated memory is built on SRAM, which has relatively low power consumption with relatively fast response. The MCU 530 may be coupled to internal or external program storage unit, such as a flash memory 532, or some other type of non-volatile memory. The flash memory 532 may be of serial type. In an embodiment, the integrated memory 530A is used as cache memory. However, there may be other purposes for the integrated memory 530A, as will be described.

However, in an embodiment, the MCU 530 may not comprise any DRAM memory, such as DDR memory. This may ensure low power consumption for a given task when compared to the power consumption of the MPU 500 for the same task. However, this may also limit the availability of features accessible when the device is running by the MCU 530.

The connections between different components of the device 100 in FIG. 5 may be wired. For example, the connections may be based on an inter-integrated circuit (I2C) bus, integrated interchip sound (I2S) bus, a serial peripheral interface (SPI) bus. The buses may utilize, e.g., RS-232, a general-purpose input/output (GPIO), and/or universal asynchronous receiver/transmitter (UART) for translating data between parallel and serial forms. For example, an I2C or an SPI bus may be set up between the MPU 500 and the MCU 530 in order to enable control and/or data communication between these two processing units.

As said, it may be advantageous to switch between the normal and the limited operation mode 210 and 212 on the basis of the power consumption and the needs of the user 110 in terms of the functionalities of the device 100. Let us next look at how the limited operation mode 212 may be obtained.

In an embodiment, the device 100 comprises at least one first memory unit which is used during the limited operation mode 210 and at least one second memory unit which is used during the normal operation mode 210, wherein the at least one second memory unit is not used during the limited operation mode 212. In an embodiment, the at least one first memory unit is of a type with a power consumption rate less than a predetermined consumption threshold, and the at least one second memory unit is of a type with a power consumption rate above the predetermined consumption threshold. In an embodiment, the type of the at least one second memory unit is DDR and the type of the at least one first memory unit is a SRAM. The size of the first memory unit may be at maximum a few tens of MBs, such as 32 MB. In an embodiment, the first memory unit may be integrated within the corresponding processing unit, such as the memories 500A, 530A in the MPU 500 or in the MCU 530, respectively.

As the SRAM may be used during the limited mode 212 and the DDR memory may be switched off, the power consumption rate during the limited mode 212 may advantageously be smaller for a given task than in the normal operation mode 210. Thus, the use of the first memory type and not the second may represent one possible type of limited operation mode 212. It needs to be noted that some tasks/functions/applications may be run in both modes 210, 212. However, some tasks/functions/applications may only be available during the normal operation mode 210 because the processing capacity of the SRAM memory which is used during the limited operation mode 212 is limited. However, at least the PAA 220 may be run during the limited operation mode 212 by applying the first memory unit.

An access to non-volatile memory unit, such as (serial) flash 502, 532, may be available during both of the modes 210, 212 for retrieving software code which runs the operating system 300, at least part of the operating system 300, or a predetermined application, such as the PAA 220. The retrieved software may then be stored to the used volatile memory unit (either the first memory unit or the second memory unit) for quicker access. In an embodiment, the accessible non-volatile memory unit may be used for storing physical exercise data during the limited operation mode 212.

In one embodiment, the device 100 comprises a low power control unit (e.g. the MCU 530) for running at least the PAA 220 during the limited operation mode 212, and a high-power control unit (e.g. the MPU 500) for running the operating system 300 during the normal operation mode 210. As indicated above, the low power control unit 530 has lower power consumption in performing a given task than the high-power control unit 500.

Figure 2C:
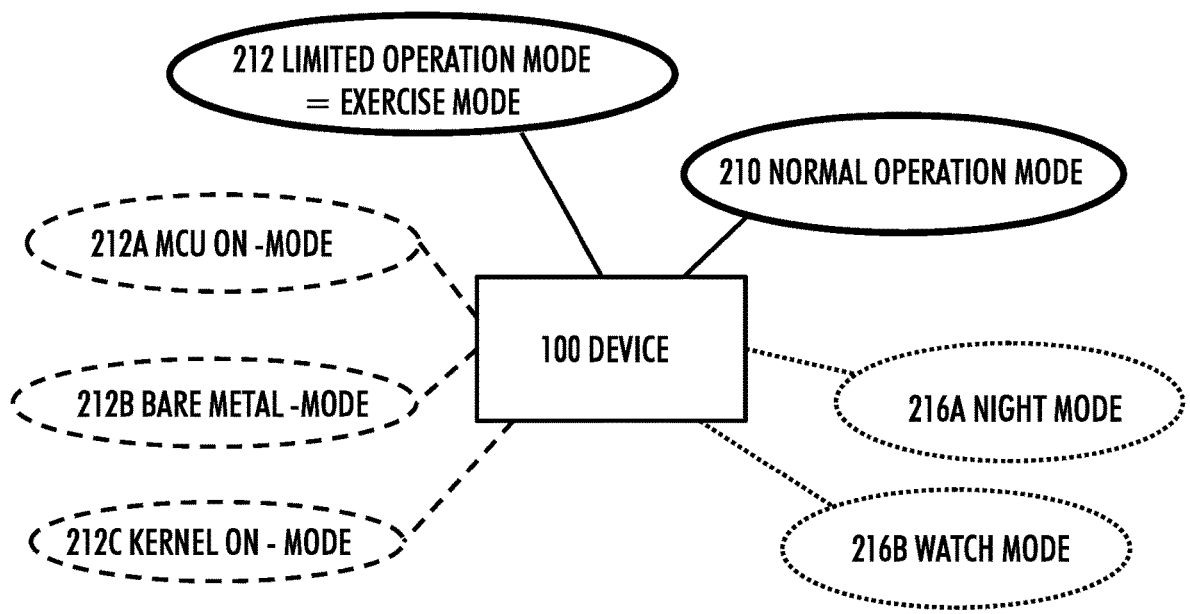
FIG. 2C shows different operation modes of the device, according to an embodiment.

In such case, the switch to the limited operation mode 212 in step 204 may comprise activating the low power control unit 530 to run at least the PAA 220 and inactivating the high-power control unit 500. In an embodiment, inactivating the MPU 500 may comprise inactivating the DDR memory accessible by the MPU 500. Thus, power consumption rate of the device 100 may be reduced. This mode may be referred as "MCU on-mode" 212A, as shown in FIG. 2C.

The MCU 530 may not be able to run the OS 300 of the device 100. This may be due to lack of sufficient memory resources: the SRAM capacity used in the MCU 530 may be too small to run the OS 300. In practice, the costs of the SRAM memory limit the size of the available SRAM memory. For example, in practice it is not feasible to provide the device 100 with SRAM memory of 512 MBs, which is needed for running the Android OS 300. In an embodiment, the kernel 302 of the operating system 300 is also not run during the limited operation mode 212A. This may be due to lack of MMU 501 in the MCU 530. The direct HW access in this mode 212A may take place via input/output pins (interface) of the MCU 530, for example, through the SPI- or I2C-buses. The MCU 530 may comprise separate HW drivers designed for the MCU 530 for this purpose. However, the MCU 530 may run a separate software (i.e. separate from the operating system 300) capable of executing the limited subset of the functionalities 104. These limited functionalities may comprise the functionalities provided PAA 220. In an embodiment, the separate program may be stored in the flash memory 532 of the device so that the MCU 530 may access the stored program. The MCU 530 may then store the program, including the PAA 220, to the SRAM integrated memory 530A of the MCU 530 for quick access and, e.g., run the PAA application 220.

In an embodiment, the separate program comprising the PAA 220 is a native application designed for the platform of the device 100. Thus, the PAA 220 is not a web application. The PAA 220 may apply only those system services required for the execution of the PAA 220. The separate program comprising the PAA 220 may also be referred to as an embedded application as it may be embedded in the corresponding processing unit.

The MPU 500 and the MCU 530 may communicate with each other to synchronize the activation of the MCU 530 and the inactivation of the MPU 500 so as to provide a smooth transition from the normal operating mode 210 to the limited operation mode 212, and vice versa.

In one embodiment, entering the limited operation mode 212 comprises inactivating (switching off) the kernel 302 and all the other layers of the operating system 300. This type of limited mode 212 may be called a "bare metal-mode" 212B shown in FIG. 2C, and it may comprise running the PAA 220 with the SRAM of the MPU 500. The PAA 220 may be stored on a non-volatile memory unit associated with the MPU 500 and downloaded to the internal memory (e.g. SRAM) 500A of the MPU 500 for quicker access with low power consumption. As the kernel 302 and the rest of the operating system 300 is inactivated, the power consumption of this "bare metal"-type of limited operation mode is smaller than if the operating system 300 or even only the kernel 302 was kept on. This is because the DDR memory of the MPU 500 with relatively high-power consumption rate may be inactivated as the OS 300 is not run. Having the bare metal mode as an option may be beneficial because if the device 100 does not comprise the MCU 530 at all, the limited power mode is nevertheless possible by entering the bare metal-mode and running the PAA 220 with the MPU 500.

In an embodiment, entering the "bare metal-mode" 212B may be performed via booting of the operating system 300 of the device 100. In this way, the running operating system 300 is first shut down. However, upon booting, instead of running the operating system's activation files, the MPU 500 may download the separate software program with limited functionalities, yet including the PAA 220, from an associated non-volatile memory, such as the flash memory 502A, to the integral SRAM 500A and run the limited program 220 with a relatively low power consumption rate. In such case, the hardware access to the HW 230 needed for the execution of the PAA 220 may be direct between the MPU 500 and the needed hardware. There may be separate HW drivers, designed for the bare metal mode, which may be used for the direct HW access.

As indicated above, the kernel 302 of the operating system 300 may not be run during the limited operation modes 212A, 212B. However, in yet one type of limited operation mode 212, namely in a "kernel on-mode" 212C, the device 100 may comprise an external memory unit, such as a volatile memory unit (e.g. a flash memory unit 502A). The device 100 may use the external memory unit in running the kernel 302 of the operating system 300. However, at least the layers of the operating system 300 above the kernel 302 and the library functions-layer 304 may be inactivated so as to avoid the need to apply the power consuming DDR memories. In an embodiment, the external memory unit may comprise, e.g. 32 MB which may be enough for running the kernel 302 but not the full OS 300. In the "kernel on-mode" 212C, the MPU 500 may be configured to run the physical activity algorithm 220 from the external ROM memory. In an embodiment, though, the MPU 500 may download the PAA 220 from the external ROM memory to the integral SRAM for quicker access.

In an embodiment, the PAA 220 may be arranged to be run by the SRAM capacity of the device 100. Therefore, the DDR memory of the device 100 need not be used and may be switched off to save power.

In an embodiment, the limited operation mode 212 may be used during the physical activity session so as to reduce the risk of power run-out during the session. From this point of view, the limited operation mode 212 may be called an exercise mode. The exercise mode may correspond to a long physical activity session, such as jogging. In an embodiment, the normal operation mode 210 may be used in a short exercise mode during which the full set of functionalities of the device 100 may be available to the user 110. In this light, the normal operation mode 210 may also be called a short exercise mode. There may be a predetermined time duration which divides a physical activity session into a short physical activity session and a (long) physical activity session.

In an embodiment, the physical activity session is any session during which physical activity may be measured. For example, sleeping may be a physical activity which may be measured in terms of activity measurement during the sleep. In an embodiment, however, the physical activity session is an exercise performed by the person 110. The exercise may be differentiated from other physical activity sessions (such as from sleeping) by defining an activity threshold (e.g. in terms of calories consumed per given time unit) which divides physical activities into exercises and non-exercises.

Let us next consider a case when the limited operation mode 212 may be triggered on. In an embodiment, the MPU 500 runs the PAA 220 initially while the device is operating under the normal operation mode 210. However, during the physical activity session, it may be determined that the current power resources of the device 100 are not enough to last until the estimated end of the current physical activity session. In such case, the MPU 500 and/or the MCU 530 may automatically perform the switch to the limited operation mode 212. Thus, the user 110 need not interact at all for the switch to take place. The switch to the limited operation mode 212 may be invisible to the user 110. In another embodiment, entering from the normal operation mode 210 to the limited operation mode 212 requires user confirmation, which the user 110 may input via the user interface (e.g. a touch display, mechanical buttons) of the device 100.

Figure 6:
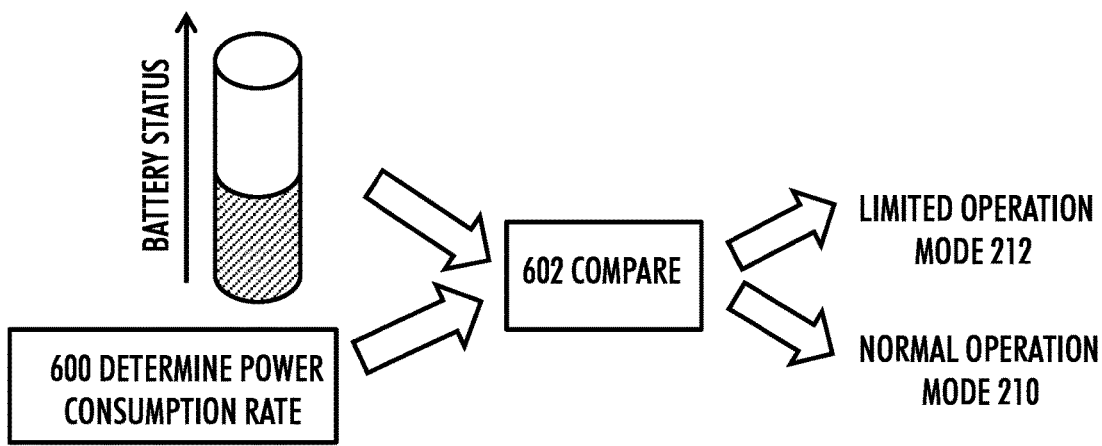
FIGS. 6 to 8 illustrate when a change between the modes may be performed, according to some embodiments.

As said, the device 100 may comprise the power supply 506 for providing power for the operation of the device 100. As shown in FIG. 6, in an embodiment, the at least one processing unit (e.g. the MPU 500) may detect the power status of the power supply 506. In step 600, the MPU 500 may further determine a current power consumption rate of the device 100. The MPU 500 may then compare in step 602 the power consumption rate to the detected power status of the battery (power supply) 506. Thereafter, the MPU 500 may, on the basis of the comparison result, decide on the switching between the normal operation mode 210 and the limited operation mode 212.

For example, if the comparison result indicates that the remaining power resources are below a predetermined battery threshold and the power consumption rate is above a predetermined consumption threshold, then the MPU 500 may decide to perform a switch to the limited operation mode 212 so as to extend the lifetime of the battery. On the other hand, if the comparison result indicates that the remaining power resources are above the predetermined battery threshold and/or the power consumption rate is below the predetermined consumption threshold, then the MPU 500 may decide to maintain the normal operation mode 210. In case the device 100 is already operating on the limited mode 212 and the comparison result indicates that the battery status is above the predetermined battery threshold, then the responsible processing unit 500 may decide to switch into the normal operation mode 210.

In an embodiment, remaining time duration until the next power supply charging may be estimated. This may be determined on the basis of history information related to battery charging. For example, it may be typical behaviour of the user 110 of the device 100 to charge the device 100 periodically, such as every night. It may be noted also that the device 100 may keep track of the current time of the day. In such case, the MPU 500 may perform the decision regarding the switching further on the basis of the remaining time duration until the next power supply charging. For example, in case it is determined that the power consumption rate is high (above the consumption threshold) and the battery level is low (e.g. below the battery threshold) but there is only a short time until the next charging is expected to take place, then the device 100 may decide to stay in the normal operation mode 210. The short time may be defined as a time that is shorter than the remaining operation time of the device 100 assuming the power consumption rate remains as it currently is. This embodiment may thus reduce unnecessary switches to the limited operation mode 212.

Figure 7:
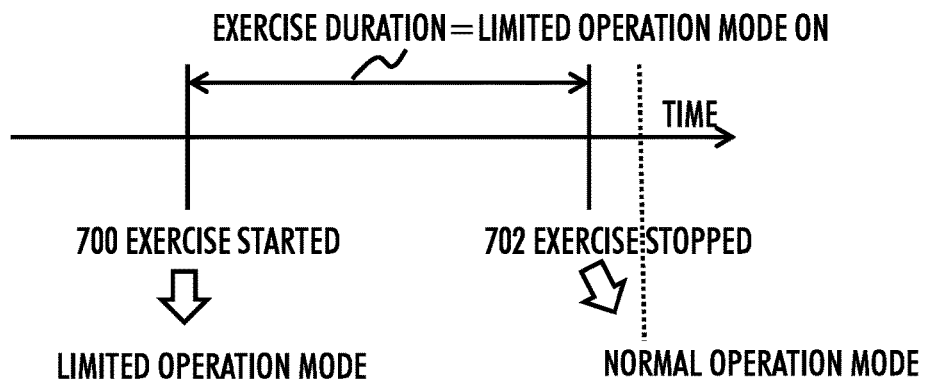

In one embodiment shown in FIG. 7, the MPU 500 may detect the beginning 700 of the physical activity session (e.g. of the exercise) and decide to switch to the limited operation mode 212 at the beginning of the physical activity session. This may provide for simplicity in the usage of the modes 210, 212. Furthermore, as the user 110 most likely needs not to use the full operating system 300 during the exercise, the switch to the limited operation mode 212 right at the beginning of the exercise may not adversely affect the user 110 but may advantageously extend the battery life of the device 100.

Figure 8:
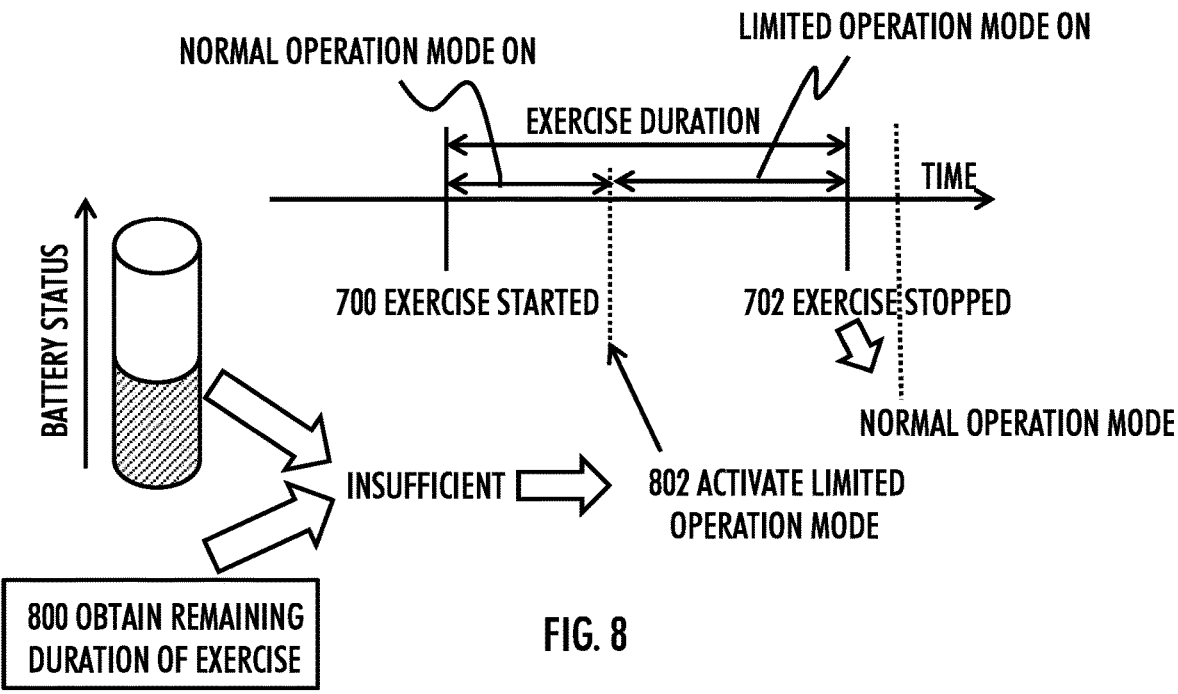

In one embodiment, as shown in FIG. 8, let us assume that the exercise has started in point 700 and the device 100 currently runs on the normal operation mode 210. During the ongoing exercise, the MPU 500 may detect the power status of the battery and in step 800 obtain the remaining duration of the ongoing physical activity session. This may be acquired in various manners, as will be explained later. Next, the MPU 500 running the OS 300 during the normal mode may compare the power status to the remaining duration of the ongoing physical activity session. On the basis of the comparison, the MPU 500 may decide whether or not to switch to the limited operation mode 212.

As an example, upon detecting, based on the comparison result, that the power status of the battery 506 is not enough to last until the end of the on-going physical activity session, the MPU 500 may decide to switch to the limited operation mode 212. In the example of FIG. 8, the comparison indicates that the battery status is insufficient to last until the end of the exercise and, thus, the MPU 500 may in step 802 determine to switch the limited mode 210 on. The MPU 500 may further detect the current power consumption level and take that into account when determining whether or not to switch to the limited operation mode 212. On the other hand, upon detecting, based on the comparison result, that the power status of the battery 506 is enough to last until the end of the on-going physical activity session, the MPU 500 may decide to remain in the normal operation mode 210.

Figure 9:
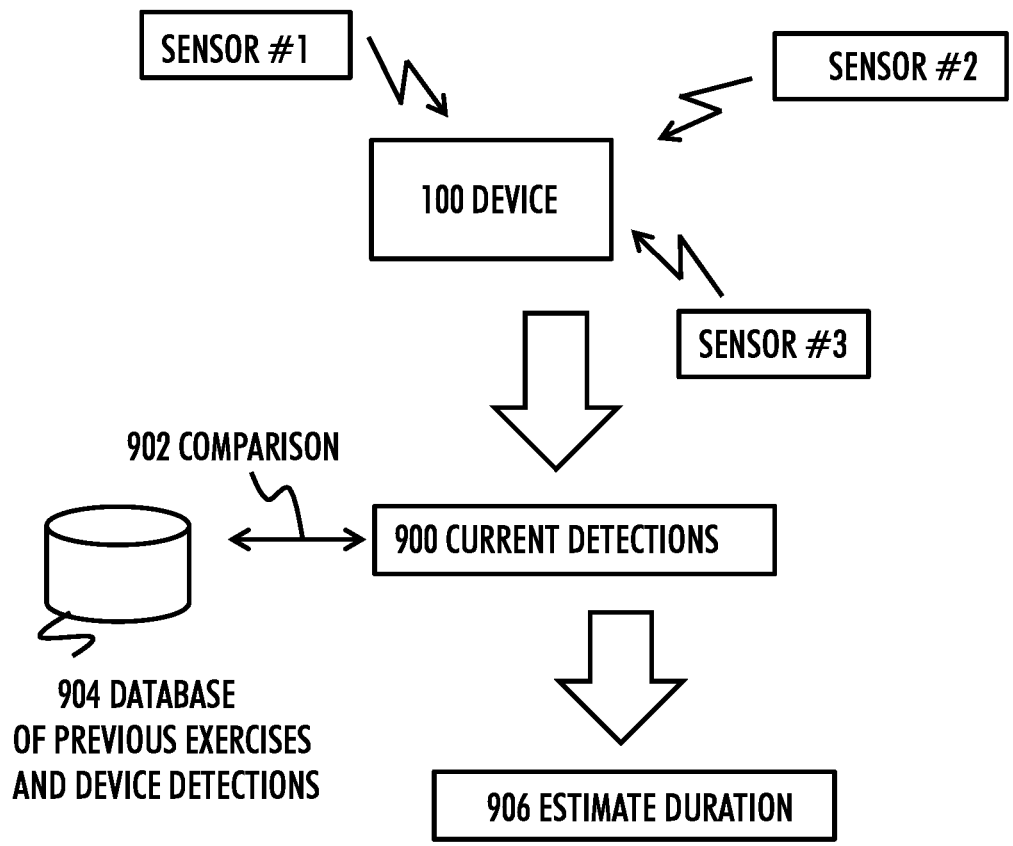
FIGS. 9 to 10 show how to estimate the remaining duration of the ongoing exercise, according to some embodiments.

In an embodiment, the device 100 may obtain the remaining duration of the ongoing physical activity session as shown in FIG. 9. The device 100 may in step 900 detect at least one physical activity sensor (#1, #2, #3) in the proximity of the device 100. The detection of the sensors may be based on identifiers transmitted by the sensors via BLT, for example. From the identifiers, the device 100 may detect that the surrounding devices are physical activity sensors.

Then the device 100 may in step 902 compare the detected at least one physical activity sensor (#1, #2, #3) to a database 904 comprising information of previous physical activity sessions and previously detected physical activity sensors. This database 904 may be stored in the ROM memory 502C of the device or in a server accessible by the device 100, for example. The database 904 may store, e.g. information on which physical activity sensors (or other surrounding devices) have been detected in which exercises and how long these exercises have lasted.

In one embodiment, the detected at least one physical activity sensor (#1, #2, #3) is not paired with the device 100 or otherwise associated with the device 100. These sensors may be sensors of other people exercising in a gym or sensors integrated to the exercise environment, for example.

In step 906, the device 100 may estimate the remaining duration of the ongoing physical activity session on the basis of the comparison result. For example, it may be that these sensors (#1, #2, #3) have been detected also in some of the previous exercises, and each time these sensors have been detected, the exercise has lasted substantially one hour. It may be that these sensors are integrated into bicycles of the gym and a typical bicycle session in the gym lasts for one hour. Then, it may be assumed that the current exercise will also last substantially for one hour.

In an embodiment, the detected at least one physical activity sensor (#1, #2, #3) is already paired with the device 100. For example, when the person starts a bike exercise, the device 100 may detect a cadence sensor. This way, the device 100 may detect, on the basis of the detected sensors, which type of exercise is being performed or is going to be performed. It may also be that certain type of sport, such as jogging, typically lasts for 45 minutes with this user 110. Therefore, it may be expected that the exercise will also now last for the same duration In one embodiment shown in FIG. 10, the device 100 may in step 1000 determine at least one property of the ongoing physical activity session. The property may be, e.g., heart activity related property, such as average heart rate or heart rate variation, or an accumulated property, such as distance elapsed, calories consumed or steps taken.

In step 1002, the device 100 may compare the determined at least one property to stored data relating to previous physical activity sessions of the same user 110. The data may be stored in a database 1004 which may be located in a non-volatile memory or in a server accessible to the device 100 over network. The database 1004 may store data that associates certain properties to certain physical activity types. For example, skiing may be characterized with certain heart activity and certain elapsed distances, whereas the corresponding characterizing features for ice hockey training may be significantly different. Therefore, the device 100 may detect which physical activity type is currently being performed on the basis of the comparison. As another example, it may be noted, that e.g. sleeping may be characterized with a relatively slow activity whereas some other physical activities, such as sports, may output a larger activity metric.

In step 1006 the device 100 may then estimate the remaining duration of the ongoing physical activity session on the basis of the comparison result. For example, based on the database 1004, it may be derived that the determined at least one property indicates that the person 110 is jogging. Further, the database 1006 may store data that indicates how long a certain physical activity with this user 110 usually lasts. Therefore, it may be possible for the device 100 to obtain an estimate of the remaining duration of the ongoing physical activity session.

In an embodiment, the database(s) 904, 1004 may locate in the Internet or separate databases accessible by the device 100. In an embodiment, the database(s) 904, 1004 may locate in the device 100 as pre-stored data.

In an embodiment, the user 110 inputs an indication of the duration of the physical activity session before starting the exercise. This may be the case when the user 110 is starting the physical activity session according to predetermined training program. The user 110 may design the training programs with the device 100 or in the web service 120, or in a separate mobile phone, and upload the designed program(s) to the device 100. As such, the duration of the exercise may be known right at the start of the exercise.

In an embodiment, the time of day and/or the day of the week is taken into account when determining the duration of the exercise. For example, on the weekends, the user 110 may perform longer trainings than during the labor days.

In an embodiment, the switch to the limited operation mode is triggered before any indication of a power shortage is detected. This may be beneficial so that the risk of running out of battery 506 is reduced.

In an embodiment, once the limited operation mode 212 is switched on, the limited mode 212 is maintained on until a predetermined duration is expired, after which the normal mode 210 is automatically triggered on. Thus, the limited operation mode 212 may be kept on for some time even after the physical activity session is over.

However, in an embodiment, as illustrated in FIGS. 7 and 8, the device 100 may detect that the physical activity session is ended. This detection may be automatic or inputted by the user 110 As a consequence, in step 702, the device 100 may enter to the normal operation mode 210. This may comprise activating all layers of the operating system 300, thereby allowing the larger set of functionalities to be run on the device 100. At the same time, however, the DDR memories may need to be activated and, thus, the power consumption may increase.

However, as illustrated in FIGS. 7 and 8, the triggering on of the OS 300 may take some time. The user 110 may find it frustrating to wait for the OS 300 to fully turn on. Therefore, in an embodiment, as shown in FIG. 11, the device 100 may estimating the ending time of the current physical activity session. This may be determined e.g. as explained with reference to FIGS. 9 and 10. Thereafter, the device 100 may in step 1100 start activating the operating system 300 at least a predetermined activation duration 1102 before the current physical activity session is to be ended, wherein the predetermined activation duration 1102 substantially corresponds to the time duration it takes for the operating system 300 to fully activate. Owing to this, the user 110 may not need to wait at all for the OS 300 to turn on, as the OS 300 may already be switched on when the exercise ends.

In an embodiment, the PAA 220 is a program, when executed, causes the device 100 to obtain physical activity data from at least one physical activity sensors associated with the device 100 and to store the received physical activity data.

The data may be stored in the device's memory, and or transferred to the server 120. In an embodiment, the network access interfaces are closed during the limited operation mode 212 so as to reduce power consumption. Therefore, the device 100 may first store the exercise physical activity data to the device's own memory and thereafter, once the normal operating mode 210 is entered and network access interfaces, such as WiFi or cellular access interfaces 546, 526, are activated, the physical activity data may be transferred to the network service 120 for storage.

In one embodiment, the physical activity data may be obtained from the device's own integrated physical activity sensors, such as GPS receiver 522, optical heart activity sensor 528, pressure sensors, temperature sensors, and motion sensors (e.g. gyroscope, accelerometer). In this case, the data may be obtained via an integral bus interface, such as the I2C bus.

Alternatively or in addition to, in an embodiment, the physical activity data may be received from at least one external physical activity sensor over wireless connection, such as BLE. These external sensors may comprise, e.g., electrical heart activity sensor, external GPS receiver, external motion sensor (e.g. an accelerometer), a cadence sensor. In one embodiment, at least one of the external sensors may be carried on the user 110. In one embodiment, at least one of the external sensors may be integrated in an exercise device used for performing the exercise, such as a gym device.

In an embodiment, there are various tasks that the PAA 220 causes the device 220 to perform. Let us now take a look at what the PAA 220, which is run in the device 100 during the limited operation mode 212, causes the device 100 to do.

In an embodiment, the physical activity algorithm causes determination of heart activity of the user on the basis of the obtained physical activity data. This may result in determination of the heart rate or the heart rate variation, for example.

In an embodiment, the physical activity algorithm causes determination of the heart rate zone of the heart rate of the person 110. The heart rate zones may be pre-determined. However, in an embodiment, the PAA 220 causes determination of the heart rate zones in the beginning of the physical activity session. The determination may take place, e.g. according to a ZoneOptimizer® functionality of Polar Electro.

In an embodiment, the physical activity algorithm causes determination of minimum and maximum values for a certain physical activity measure. Such measure may be, e.g. heart rate, altitude (e.g. above a sea level), speed, to mention only a few non-limiting examples.

In an embodiment, the physical activity algorithm causes determination of the distance elapsed during the physical activity session on the basis of the obtained physical activity data, such as on the GPS or other motion data.

In an embodiment, the physical activity algorithm causes determination of speed during the physical activity session on the basis of the obtained physical activity data, such as GPS data.

In an embodiment, the physical activity algorithm causes determination of calories consumed during the physical activity session on the basis of the obtained physical activity data. In an embodiment, the physical activity algorithm causes determination of fata consumption of the consumed calories on the basis of the obtained physical activity data.

In an embodiment, the physical activity algorithm causes determination of an activity metric on the basis of the obtained physical activity data. The activity metric may be based on motion data from the motion sensors, such as from the accelerometer. The activity metric may indicate how active the user 110 was during the physical activity session. In an embodiment, this activity metric is determined while the person 110 is in a sleep, thereby obtaining a measure of how well the person has rested.

In an embodiment, the physical activity algorithm causes determination of training load caused by the physical activity session on the basis of the obtained physical activity data.

In an embodiment, the physical activity algorithm causes determination of cadence during the physical activity session on the basis of the obtained physical activity data.

In an embodiment, the physical activity algorithm causes determination of skin temperature on the basis of the obtained physical activity data. This type of physical activity data may be received from a temperature sensor.

In an embodiment, the physical activity algorithm causes determination of orientation on the basis of the obtained physical activity data, such as magnetometer data.

Therefore, in an embodiment, the functionalities 104 available in the limited operation mode 212 include physical activity data processing. In an embodiment, the functionalities 104 available in the limited operation mode 212 include sensor fusion operations to utilize data from many different physical activity sensors.

In an embodiment, the functionalities 104 available in the limited operation mode 212 include low-range communication capability. This may be in order to receive physical activity data from the external physical activity sensors. The communication may apply, e.g., BLT or BLE unit 520 of FIG. 5.

In an embodiment, the functionalities 104 available in the limited operation mode 212 include location tracking on the basis of GPS data received by block 522 of FIG. 5, for example.

In an embodiment, the functionalities 104 available in the limited operation mode 212 include audio guidance so that the user 110 may hear, e.g., when the heart rate exceeds a certain level.

In an embodiment, the functionalities 104 available in the limited operation mode 212 includes mobile control (e.g. to control audio player of the mobile phone).

Let us further look at which functionalities may be and may not be available during the limited operation mode 212 with reference to Table 1. It should be noted though that Table 1 is merely an example configuration of the functionalities available in different modes. A plurality of different kinds of configurations, each providing different functionalities in different modes, are available and within the scope of the disclosed subject matter.

A cross in the column corresponding to the limited operation mode 212 (i.e. the exercise mode) indicates which features may be available to the device 100 in the limited operation mode 212. The table further indicates which features are available for the device 100 during the normal operation mode 210. As seen, the functionalities of the device 100 may be significantly reduced in the limited operation mode 212 in order to reduce power consumption of the device 100.

TABLE 1

Functionalities available during different modes

| | | Operating modes | | | |
|---|---|---|---|---|---|
| | FEATURES | Night mode 216A | Watch mode 216B | Normal mode 210 | Limited mode 212 |
| SMART WATCH | LISTEN TO IT | Embedded MP3 music | | | X | |
| | | Notifications: Email sender ID and subject | | X | X | |
| | | Incoming caller ID | | X | X | |
| | | Text message sender ID | | X | X | |
| | | Silent your phone | | X | X | X |
| | | Music controls for mobile phone | | X | X | X |
| | | Find your phone | | X | X | |
| | | Answer/make calls via wireless headset | | X | X | |
| | | Tap screen to answer incoming call | | X | X | |

TABLE 1-continued

Functionalities available during different modes

| | | | Night mode 216A | Watch mode 216B | Normal mode 210 | Limited mode 212 |
|---|---|---|---|---|---|---|
| | | Call-back feature for missed calls from wrist unit | | | X | |
| | | Remote control for phone camera for action video shooting | | | X | |
| | SOCIAL FLOW CONNECTION | Real time connectivity | | X | X | |
| | | Service notifications | | X | X | |
| | | Real time social connectivity | | X | X | |
| | CONNECTIVITY | Flow and Flow app support | | X | X | |
| | | USB (OR QI wireless CHARGING) | | X | X | |
| | | NFC | | X | X | |
| | | WIFI | | | X | |
| | | BLT, BLE | | X | X | X |
| | TOUCH COLOR DISPLAY | | | X | X | |
| | GESTURE BASED WAKE UP | | X | X | X | |
| | 3rd PARTY API FOR DEVELOPERS | API for external developers | | | X | |
| | | Released apps need Polar approval for device compatibility | | | X | |
| | 3rd PARTY APPS | Download 3rd party apps from Web | | | X | |
| POLAR SMART COACHING | INTEGRATION WITH HEALTH CLUBS | NFC for easy identification | | X | X | |
| | | Training diary info from machines | | | X | |
| | | Compatibility with OEM module | | X | X | X |
| | | Compatible with passive NFC tags | | | X | |
| | SMART COACHING OHAS | Adaptive training program | | | X | X |
| | | Automatically synced training plans and target training. | | | X | X |
| | | Strength training | | | X | X |
| | | Music guided heart rate training | | | X | |
| | SMART COACHING STRAP | FIT/FAT (strap) | | | X | X |
| | | Target training (strap) | | | X | X |
| | | Training zones for guidance (strap) | | | X | X |
| | | Relaxation test (strap) | | | X | |
| | | Fitness test (Strap) | | | X | |
| | FOLLOWS YOU | Wellness Forecast | | | X | |
| | DAILY ACTIVITY | 24/7 total calories | X | X | X | X |
| | | 24/7 daily activity measurement and personalized goal | X | X | X | X |
| | | Activity guide and benefit | | | X | |
| | | Sleep analysis | X | | X | |
| | | Activity Benefit | | X | X | X |
| | | Inactivity alerts with vibration alert | | X | X | |
| | ADAPTIVE MOTION RECOGNITION | Accelerometer based sport/motion recognition for enhanced workout tracking and guidance | | | X | X |
| | FEEL IT | Haptic training feedback and guidance | | | X | X |
| | TRACK EATING HABITS | Easy input for marking eating | | | X | |
| | RUN WITH IT | GPS route, speed and distance | | | X | X |
| | | Accelerometer based indoor speed and distance | | | X | X |
| | | Integration with Apps | | | X | X |
| | AUDIO GUIDANCE | Embedded audio Guidance | | | X | |
| | STAY CONNECTED | See on your device your personal trainer's guidance before training starts | | | X | |
| | 3rd PARTY DEVICE CONNECTIVITY | External devices to provide health related data e.g. body composition etc. | | | X | |
| | | e.g. Food diary, Body composition measurement | | | X | |
| | | Set a how much you have time to train and let the device maximize your health and fitness benefit. | | | X | |

Table 1 also shows other types of limited operation modes 212, such as a night mode 216A and a watch mode 216B of FIG. 2C. The table may indicate which features may be available during those modes. These modes may be seen as subtypes of the limited operation mode 212 as the functionalities of the device 100 are limited to only a sub-set of functionalities compared to the normal mode 210, which may be called a fiddling mode as well.

In an embodiment, the night mode 216AC is used during predetermined times, such as during nights. Typically, a user does not need many functionalities of the device 100 during nights, so the device 100 may be switched to the night mode 216A. However, for example the activity of the person may be monitored also during the night by running the PAA 220. In an embodiment, the features available during the night mode include sleep analysis on basis of activity sensing (e.g. monitoring activity of the user 110 while asleep with the motion sensors), calorie consumption algorithm for determining the amount of calories consumed and watch functionality.

In an embodiment, the watch mode 216B may be used when the full functionality of the device 100 is not needed and the user 110 needs to, at least, keep track of the time. In the watch mode, the MPU 500 may be inactive and the application needed may be run with the MCU 530. This may provide power savings. Further, only a small amount of memory is needed to be active as the features are limited. In an embodiment, the features available during the watch mode include: watch, wireless interface (e.g. for interacting with external devices, such as with a paired mobile phone, on the BLE technology), mobile control (e.g. controlling audio player of the mobile device) and the user interface of the device.

In an embodiment, the functionalities not available in the limited operation mode 212 include a touch sensitivity of the display 102 of the device 100. This may be beneficial as, though the touch sensitive display 102 is user friendly, such display causes high power consumption even though it may not be typically used during the exercise. Therefore, in order to save the power, the touch sensitivity may be switched off with the touch controller 510 upon entering the limited operation mode 212. It may be noted also tis some embodiments, the display 102 may be driven with the MCU 530 in the limited operation mode 212, as shown in FIG. 5. The MCU 530 may not have access to the touch controller 510.

In an embodiment, when the touch sensitivity function is switched off, mechanical user interface, such as mechanical buttons 106, of the device may be automatically activated for allowing the user to control the device.

In an embodiment, the functionalities not available in the limited operation mode 212 include social media support. This may be because detecting and displaying social media updates may consume power of the battery 506. In an embodiment, a mobile phone of the user 110 is connected to the social media server and detects the updates. The mobile phone then transmits an indication to the device 100, such as a wrist watch, and the device 100 then notifies the user 110. Although, the device 100 may not need to be itself connected to the social media servers, the device 100 may need to be able to detect notification signals from the mobile phone and this may drain power of the battery 506.

In an embodiment, the functionalities not available in the limited operation mode 212 include call and message support. Similarly, as in the case of social media support, listening to notification signals from the mobile phone related to incoming calls, may unnecessarily use battery resources. Typically, during an exercise, the user 110 is not interested in receiving notifications of call, emails, messages, or social media updates.

In the normal operation mode 210, some features available may include at least a wireless interface GPS reception, executing fitness test algorithm, use of integrated audio player of the device 100.

As said, the limited operation mode 212 may thus advantageously result in lower power consumption rate that the normal operating mode 210. In an embodiment, the limited exercise mode 212 may be seen as a state where the device 100, such as a smart watch, actively monitors the physical activity of the user 110. During this mode numerous features may be enabled for measuring, processing, recording, and analysing data of interest related to the user activity. These features of the exercise mode may affect the battery 506 life-time and therefore restrict the time duration that the device 100 may operate in such exercise mode (i.e. in the limited operation mode 212).

In an embodiment, the device 100 may dynamically limit the usage of at least one physical activity-related functionality during the limited operation mode 212. Thus, there may be predetermined subset of functionalities available for the device 100 in the start of the limited operation mode 212. These functionalities may have a predetermined manner of usage. For example, the GPS receiver 522 may be arranged to provide a location sample periodically once per five seconds. However, the device 100 may automatically limit the usage of at least one function in real-time during the physical activity session.

In an embodiment, the limitation comprises at least one of the following: decreasing the sampling rate of physical activity data corresponding to the physical activity-related functionality, preventing the usage of the physical activity-related functionality. Thus, looking at the GPS reception—example, the device 100 may completely switch off the GPS data reception functionality by switching off the GPS receiver 522 in order to save power, or the device 100 may decrease the sampling rate, such as take samples only once per ten seconds, for example. Both manners result in less power consumption by this physical activity related functionality.

Table 2 shows example physical activity features which usage may be narrowed down. As shown there are many different features which may be either enabled or disabled according to current needs or which may be limited in performance so as to provide longer life time for the battery 506.

Table 2 lists two different groups of limitation actions: feature limiting and performance limiting. Feature limiting may completely disable the features in favor of other features which are considered of more relevance or major advantage to the user 110. Hence, some initially available features may be later disabled in order to provide other features to be active a longer period of time. On the other hand, performance limiting may denote a trade-off decision between delivering a feature to its full extend or limiting it to some degree in order to run it for a longer period while still providing a tangible benefit to the user 110.

Also, in an embodiment, the amount of data shown on the display 102 may be reduced. The training screens are screens which the user 110 may have pre-set to the device 100. Different screens may be switched during one type of exercise and different screens may be available for different exercises. The device 100 may comprise a power saving screen among the training screens. The power saving screen may comprise less data to be shown on the display 102 or outputted to the user 110. The device 100 may then switch the power saving screen once it is determined that power saving of the device 100 is to be performed.

TABLE 2

Example features available during the limited operation mode and how the usage of the features may be limited.

| Feature | Feature limiting | Performance limiting | |
|---|---|---|---|
| Vibration | Enable/Disable | Decrease intensity | Decrease pulse duration |
| Sounds | Enable/Disable | Decrease volume | Decrease pulse duration |
| Backlight | Enable/Disable | Decrease brightness | Decrease light duration |
| GPS | Enable/Disable | Decrease sample rate | Intermittent use, possibly compensated with compass, barometer and/or inertial sensors |
| Compass | Enable/Disable | Decrease sample rate | Intermittent use, possibly compensated with inertial sensors |
| Barometer | Enable/Disable | Decrease sample rate | Intermittent use, possibly compensated with inertial sensors |
| Inertial sensors | Enable/Disable | Decrease sample rate | Intermittent use, possibly compensated with inertial sensors |
| External sensors | Enable/Disable | Decrease sample rate | |
| Training screens | Enable/Disable | Decrease refresh frequency | Remove amount of data shown |

Figure 12:
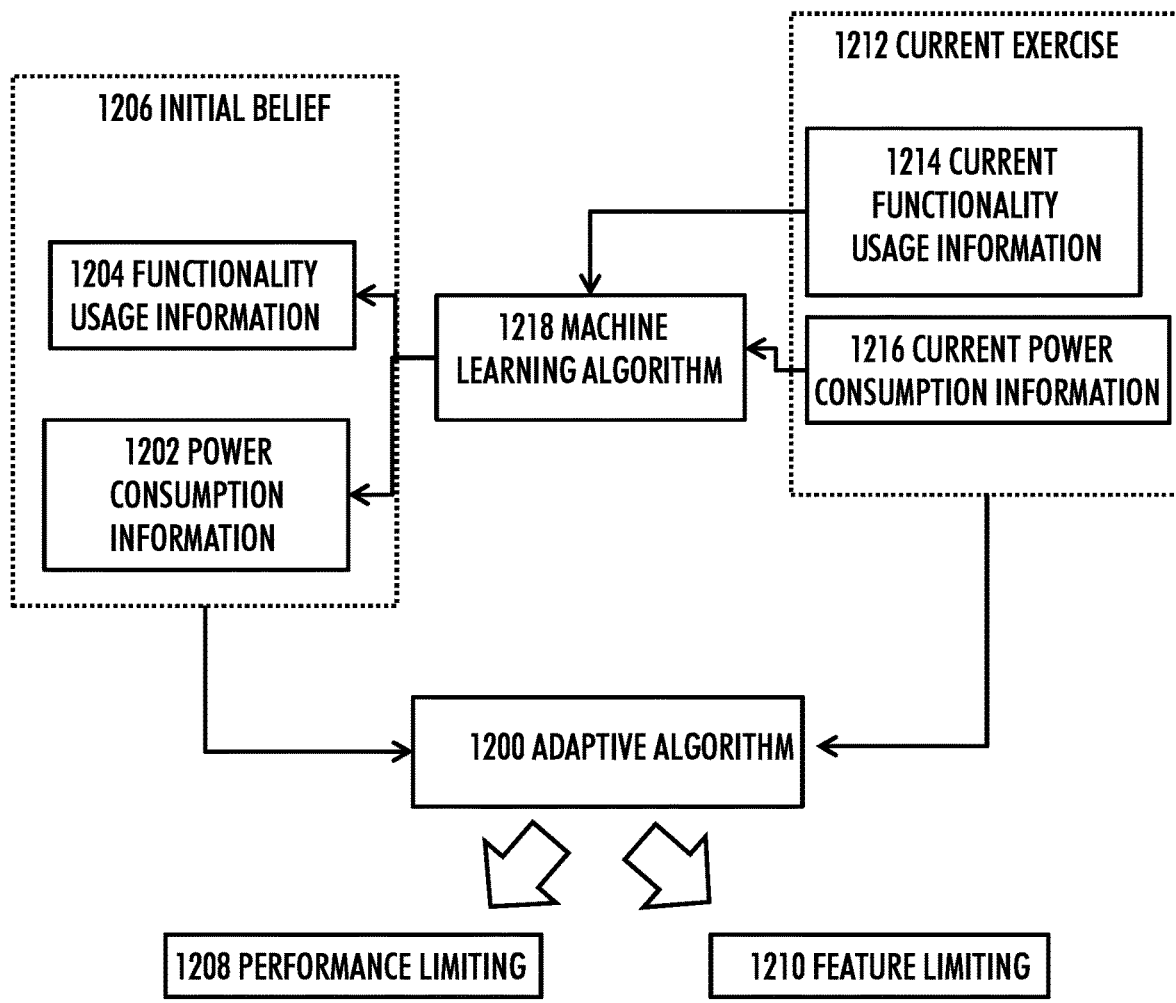
FIG. 12 depicts how a usage limitation may be decided, according to an embodiment.

In an embodiment, an adaptive algorithm 1200 shown in FIG. 12 is utilized to make real-time decisions that may provide longer training times for the user without risking the end of the battery life. These decisions may have a direct impact on the overall power consumption of the device 100, leading to longer available exercise periods to users 110. By understanding and learning about how each user 110 utilizes the device 100 features during the exercise mode 212 and measuring them against the power consumption in real-time, the device 100 make decisions that help to provide longer training periods.

At the beginning, the adaptive algorithm 1200 uses only predefined information about how the different features and settings correlate to power consumption. This is referred in the FIG. 12 as power consumption information 1202. This power consumption information 1202 may be preconfigured in the memory of the device 100. The power consumption information 1202 may indicate the power consumption contribution of different features and sensors. For example, the information 1202 may indicate how much power the GPS requires when the sampling rate is 1 Hz. Further, the power consumption information 1202 may also indicate the power enhancement generated by each available feature limiting and performance limiting decision of Table 2, for example.

In an embodiment, the power consumption information 1202 may also indicate battery discharge behavior (i.e. how the power consumption develops) during typical exercises of the user 110 in the exercise mode 212. The typical battery discharge behavior during for this user 110 may be based on history data of prior exercises of the user 110.

Figure 10:
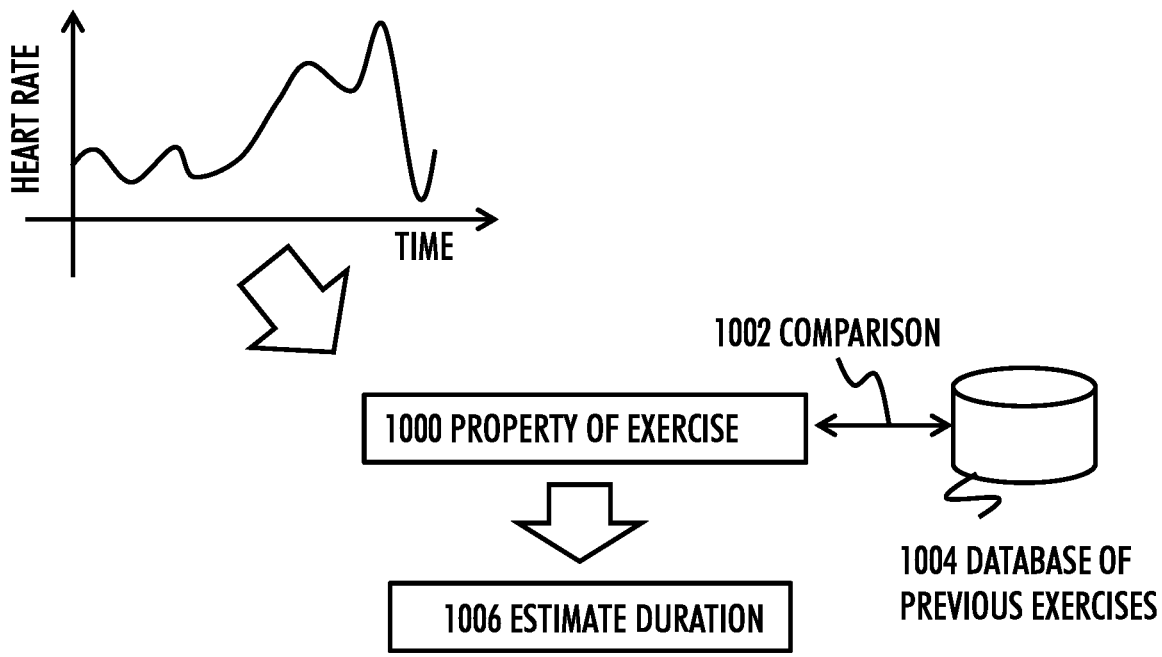
Figure 11:
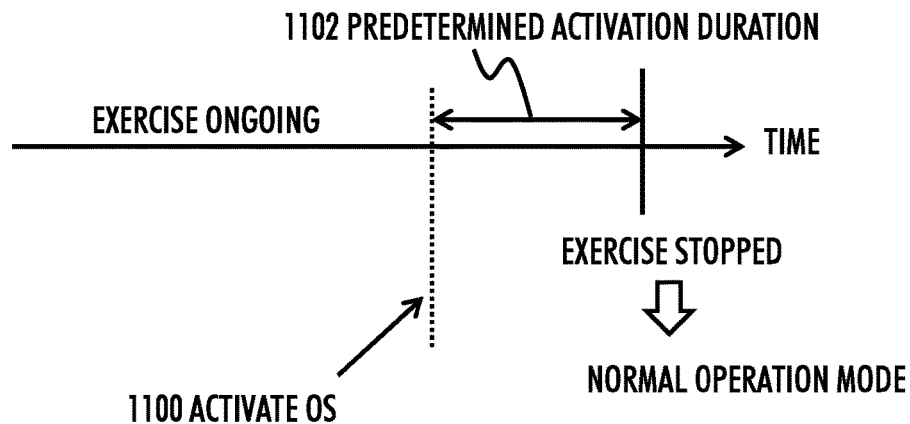
FIG. 11 illustrates switching back to normal operation mode, according to an embodiment.

In an embodiment, an estimate for the required exercise duration may also be determined, possible in one of the manners as indicated with reference to FIGS. 9 and 10 or based on user input.

Further, there may be functionality usage information 1204 stored in the device 100. The functionality information 1204 may indicate which physical activity-related functionalities are typically used during the physical activity session performed by the user 110. The data 1204 may be based on history data of previous exercises performed by this user 110 (stored in the device 100 or in the web service 120).

In an embodiment, the data 1204 may thus indicate how the user 110 is expected to use the features of the device 100 for a given type of sport. The usage of the features may depend on various manners. In an embodiment, the usage depends on the expected exercise duration. In an embodiment, the usage depends on the type of the sport being performed. This may be indicated on the basis of a sport profile. In an embodiment, the usage of the various available features depends on the time of day and/or the day of the week. In an embodiment, the usage of the various available features depends on preceding exercises performed during a given time window (such as during the current and the previous week).

As a result, an initial belief 1206 is composed by data from usage information 1204 as well as battery and power consumption information 1202. The adaptation algorithm 1200 may then, on the basis of the initial belief 1206, decide whether to perform performance limiting actions 1208 or feature limiting actions 1210 (some of which are listed in Table 2), so as to ensure that the battery power lasts until the end of the exercise.

In an embodiment, the device 100 may detect the current power status of the battery 506, estimate the remaining duration of the ongoing exercise; and upon detecting that the current power status of the battery 506 is not enough to last until the end of the on-going exercise on the basis of the information 1202, 1204, dynamically limit the usage of at least one physical activity related functionality of the device 100.

In an embodiment, the device 100 may obtain the power consumption information 1202 and the functionality usage information 1204. On the basis of the received information 1202, 1204, the device 100 may determine the at least one physical activity-related functionality whose usage is to be limited. For example, the device 100 may decide that temperature sensor may be switched off as the temperature of the skin is not typically needed for analysis for this person 110 and for this type of sport.

In an embodiment, there is a predetermined order of physical activity related functions. This order may be used in determining the function which usage is to be limited. In an embodiment, the order (list) is sport type-specific so that the order for ice hockey may be different than the order for jogging. This may be beneficial as different type of data may be important in different type of sports.

In an embodiment, the device 100 may use corresponding data 1214 and 1216 from the current exercise (i.e. physical activity session) 1212 in deciding about the limitation actions (1208, 1210). For example, it may be that the initial belief 1206 implies that GPS receiver 522 is not used in a biking exercise but the distance information is obtained wirelessly from a distance sensor of the bike. However, the current functionality usage information 1214 may indicate that GPS is not used instead or in addition to the bike's own external sensor. Then, the decision to limit the features may be different than in case the GPS sensor 522 was not used.

As another example, in case the current power consumption information indicates that the power level of the battery 506 is sufficient with respect to the current power consumption, then there may not be any need to limit the usage of the features, although the initial belief might indicate that the some feature should be e.g. disabled in this specific type of physical activity session.

In an embodiment, the device 100 may apply machine learning algorithm 1218 in order to complement the initial belief 1206 with feedback from the corresponding data 1214, 1216 from the current exercise (i.e. physical activity session) 1212. In an embodiment, the power consumption information 1202 and the functionality usage information 1204 are updated after each physical activity session 1212. This may take place feeding the current functionality usage information 1214 and the current power consumption information 1216 to the machine learning algorithm 1218 in order to further expand the initial belief 1206 and therefore gather more knowledge about user requirements during the exercise mode 212. As the initial belief 1206 continues to grow based on the feedback from past exercises 1212, the device 100 may better adapt and anticipate the requirements of each individual user 110 and of each individual exercise type.

In an embodiment, the device 100 may further detect a profile of the ongoing physical activity session. The profile may indicate user preferences for each type of sports being performed. The user 110 may have, in the web service 120, inputted the sport profile for each type of sport he/she typically performs. The sport profile may be used for deriving the information 1204 as well. The sport profile may further define which type of data is to be shown on the display 102 of the device 100 during the exercise. The sport profile may also indicate which types of features and sensors are to be applied for each sport. The detection of the sport profile may be made via a user input in the beginning of the exercise, or via the detection of the sport type being performed (e.g. as illustrated in FIGS. 9 and 10).

The device 100 may then determine which physical activity-related functionalities are needed during the limited operation mode 212 on the basis of the detected exercise profile. E.g. indoor sports do not apply GPS receiver 522, whereas outdoor sports may do so. Thereafter, the device 100 may run the determined physical activity-related functionalities during the limited operation mode 212 so as to ensure that all the features needed by the user 110 are available.

In an embodiment, the device 100 may inactive all the other features which the user 110 does not need during the physical activity session in the limited operation mode 212 so as to minimize the risk of running out of the battery.

In an embodiment, the device 100 determines the temperature of the device 100 and/or the ambient temperature. The device 100 may also obtain temperature information indicating how the temperature affects the power consumption rate of the device 100. This information may be pre-stored to the device 100 or fetched from the web. Thereafter, the device 100 may decide whether or not to perform functional limitations on the basis of the determined temperature and the obtained temperature information. In an embodiment, this decision may result in a switch between the limited operation mode 212 and the normal operation mode 210, limiting the availability of certain features or limiting the performance of certain features (see Table 2). When making the decision, the device 100 may be operating either in the limited operation mode 212 or in the normal operation mode 210.

In an embodiment, the device 100 comprises an ambient light sensor 534 (in FIG. 5) and the device 100 may determine the intensity of the ambient light. On the basis of the detection, the device 100 may adjust the brightness of the display 102. This may result in saving power of the device 102 as a bright display 102 need not be used in dark conditions, for example.

Let us then take a look at some power consumption related issues of the device 100 in different modes with reference to Table 3. Again, it should be noted that the values given in Table 3 merely example values depending on the configuration of the available functionalities in a given mode. It may be assumed here that the MCU on-mode is used for the limited operation mode 212 where the MPU 500 is hibernating and the MCU 530 is running the PAA 220.

TABLE 3

Power consumption of different type of modes.

| | | | Night mode 216A | Watch mode 216B | Normal mode 210 | Limited mode 212 |
|---|---|---|---|---|---|---|
| HARDWARE CONFIGURATION | Status | MCU running the physical activity algorithm and display (<3 mA) | X | X | | X |
| | | MCU running sensoring (<0.3 mA) | X | X | X | X |
| | | MPU running applications and touch display (10 . . . 200 mA) | | | X | |
| | | MPU hibernating (0.1 mA) | X | X | | X |
| | Power budget target | 400 mAh battery | | 2 mA | 200 mA | 40 mA |

Thus, as shown on the last row, the power consumption of the normal mode 210 is 200 mA which is much larger than the power consumption of the limited mode 212, or of the night mode or the watch mode, which may be seen as sub-types of the limited operation mode 212 with even less power consumption due to more restrained features.

As used in this application, the term 'circuitry' refers to all of the following: (a) hardware-only circuit implementations, such as implementations in only analog and/or digital circuitry, and (b) combinations of circuits and soft-ware (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. Coding of software for carrying out the embodiments as shown and described is well within the scope of a person of ordinary skill in the art.

Even though the disclosed subject matter has been described above with reference to an example according to the accompanying drawings, it is clear that the disclosed subject matter is not restricted thereto but can be modified in several ways within the scope of the appended claims. Therefore, all words and expressions should be interpreted broadly, and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

What is claimed is:

1. A smartwatch comprising:
   a motion sensor configured to measure a motion;
   a GPS receiver configured to receive a GPS signal;
   an optical heart activity sensor configured to optically measure a heart activity;
   a touch sensitive color display configured to act as a user interface;
   a high-power processing unit configured to, during a normal operation mode, run an operating system, control functionality of the touch sensitive color display, and measure physical activity using data obtained from the motion sensor, data obtained from the GPS receiver and the data obtained from the optical heart activity sensor; and
   a low power processing unit configured to,
      during a watch operation mode, run a watch configured to keep track of the time, run a physical activity algorithm, and measure physical activity using data obtained from the motion sensor, and
      during a limited operation mode, measure physical activity using data obtained from the motion sensor, data obtained from the GPS receiver and the data obtained from the optical heart activity sensor,
   wherein the low power processing unit has a lower power consumption in performing a given task than the high-power processing unit.

2. The smartwatch of claim 1, wherein, to switch from the normal operation mode to the watch operation mode, the low power processing unit is configured to be activated to run the watch and run the physical activity algorithm, and the high-power processing unit is configured to be inactivated.

3. The smartwatch of claim 2, wherein, to switch from the normal operation mode to the watch operation mode, the GPS receiver is configured to be switched off, and the optical heart activity sensor is configured to be switched off.

4. The smartwatch of claim 1, wherein, to switch from the normal operation mode to the watch operation mode, the touch sensitive color display is configured to be switched off.

5. The smartwatch of claim 1, wherein, to switch from the normal operation mode to the limited operation mode, the touch sensitive color display is configured to be switched off.

6. The smartwatch of claim 1, further comprising a wireless interface, the high-power processing unit being configured to interact with an external paired mobile phone via the wireless interface during the normal operation mode.

7. The smartwatch of claim 1, further comprising a wireless interface, the low power processing unit being configured to interact with an external paired mobile phone via the wireless interface during the watch operation mode.

8. An apparatus comprising:
   an interface to a motion sensor configured to measure a motion, to a GPS receiver configured to receive a GPS signal, to an optical heart activity sensor configured to optically measure a heart activity, and to a touch sensitive color display configured to act as a user interface;
   a high-power processing unit configured to, during a normal operation mode, run an operating system, control functionality of the touch sensitive color display, and measure physical activity using data obtained from the motion sensor, data obtained from the GPS receiver and the data obtained from the optical heart activity sensor; and a low power processing unit configured to, during a watch operation mode, run a watch configured to keep track of the time, run a physical activity algorithm, and measure physical activity using data obtained from the motion sensor, and during a limited operation mode, measure physical activity using data obtained from the motion sensor, data obtained from the GPS receiver and the data obtained from the optical heart activity sensor, wherein the low power processing unit has a lower power consumption in performing a given task than the high-power processing unit.

9. The apparatus of claim 8, wherein, to switch from the normal operation mode to the watch operation mode, the low power processing unit is configured to be activated to run the watch and run the physical activity algorithm, and the high-power processing unit is configured to be inactivated.

10. The apparatus of claim 9, wherein, to switch from the normal operation mode to the watch operation mode, the GPS receiver is configured to be switched off, and the optical heart activity sensor is configured to be switched off.

11. The apparatus of claim 8, wherein, to switch from the normal operation mode to the watch operation mode, the touch sensitive color display is configured to be switched off.

12. The apparatus of claim 8, wherein, to switch from the normal operation mode to the limited operation mode, the touch sensitive color display is configured to be switched off.

13. The apparatus of claim 8, further comprising a wireless interface, the high-power processing unit being configured to interact with an external paired mobile phone via the wireless interface during the normal operation mode.

14. The apparatus of claim 8, further comprising a wireless interface, the low power processing unit being configured to interact with an external paired mobile phone via the wireless interface during the watch operation mode.

15. A method comprising:

supporting a normal operation mode during which a high-power processing unit is running an operating system, controlling functionality of a touch sensitive color display, and measuring physical activity using data obtained from a motion sensor, data obtained from a GPS receiver and data obtained from an optical heart activity sensor;

supporting a watch operation mode during which a low power processing unit is running a watch to keep track of the time, running a physical activity algorithm, and measuring physical activity using data obtained from the motion sensor; and supporting a limited operation mode during which a low power processing unit is measuring physical activity using data obtained from the motion sensor, data obtained from the GPS receiver and data obtained from the optical heart activity sensor, wherein the low power processing unit has a lower power consumption in performing a given task than the high-power processing unit.

16. The method of claim 15, wherein, to switch from the normal operation mode to the watch operation mode, activating the low power processing unit to run the watch and run the physical activity algorithm, and inactivating the high-power processing unit.

17. The method of claim 16, wherein, to switch from the normal operation mode to the watch operation mode, switching off the GPS receiver, and switching off the optical heart activity sensor.

18. The method of claim 15, wherein, to switch from the normal operation mode to the watch operation mode, switching off the touch sensitive color display.

19. The method of claim 15, wherein, to switch from the normal operation mode to the limited operation mode, switching off the touch sensitive color display.

20. The method of claim 15, further comprising supporting the normal operation mode during which the high-power processing unit is interacting with an external paired mobile phone via a wireless interface.

21. The method of claim 15, further comprising supporting the watch operation mode during which the low power processing unit is interacting with an external paired mobile phone via a wireless interface.

* * * * *